(12) United States Patent
Levin et al.

(10) Patent No.: US 6,946,473 B2
(45) Date of Patent: Sep. 20, 2005

(54) PREPARATION AND USE OF ACETYLENIC ORTHO-SULFONAMIDO AND PHOSPHINIC ACID AMIDO BICYCLIC HETEROARYL HYDROXAMIC ACIDS AS TACE INHIBITORS

(75) Inventors: Jeremy I. Levin, New City, NY (US); James M. Chen, San Ramon, CA (US); Xue-Mei Du, Valley Cottage, NY (US); Jay D. Albright, Nanuet, NY (US); Arie Zask, New York, NY (US)

(73) Assignee: Wyeth Holdings Corporation, Madison, NJ (US)

( * ) Notice: Subject to any disclaimer, the term of this patent is extended or adjusted under 35 U.S.C. 154(b) by 0 days.

(21) Appl. No.: 10/390,515

(22) Filed: Mar. 17, 2003

(65) Prior Publication Data
US 2003/0208066 A1 Nov. 6, 2003

Related U.S. Application Data

(63) Continuation of application No. 09/492,978, filed on Jan. 27, 2000, now abandoned.
(60) Provisional application No. 60/198,221, filed on Jan. 27, 1999.

(51) Int. Cl.[7] .................. C07D 471/04; C07D 498/04; C07D 513/04; A61K 31/437; A61P 19/02
(52) U.S. Cl. .................. 514/301; 514/302; 514/303; 514/313; 546/114; 546/115; 546/120; 546/162
(58) Field of Search .................. 514/301, 302, 514/303, 313; 546/114, 115, 120, 162; 544/114, 115, 120, 162

(56) References Cited

U.S. PATENT DOCUMENTS

| | | | |
|---|---|---|---|
| 5,455,258 A | 10/1995 | MacPherson et al. | |
| 5,506,242 A | 4/1996 | MacPherson et al. | |
| 5,552,419 A | 9/1996 | MacPherson et al. | |
| 5,606,063 A | 2/1997 | Harrison et al. | |
| 5,753,653 A | 5/1998 | Bender et al. | |
| 5,770,624 A | 6/1998 | Parker | |
| 5,804,593 A | 9/1998 | Warpehoski et al. | |
| 5,817,822 A | 10/1998 | Nantermet et al. | |
| 5,929,097 A | 7/1999 | Levin et al. | |

FOREIGN PATENT DOCUMENTS

| | | |
|---|---|---|
| DE | 19542189 | 5/1997 |
| EP | 606046 | 12/1993 |
| EP | 757037 | 7/1996 |
| EP | 757984 | 8/1996 |
| EP | 803505 | 4/1997 |
| WO | WO 9535275 | 12/1995 |
| WO | WO 9535276 | 12/1995 |
| WO | WO 9600214 | 1/1996 |
| WO | WO 9627583 | 9/1996 |
| WO | WO 9633172 | 10/1996 |
| WO | WO 9718194 | 5/1997 |
| WO | WO 9719068 | 5/1997 |
| WO | WO 9720824 | 6/1997 |
| WO | WO 9722587 | 6/1997 |
| WO | WO 9727174 | 7/1997 |
| WO | WO 9745402 | 12/1997 |
| WO | WO 9803166 | 1/1998 |
| WO | WO 9807697 | 2/1998 |
| WO | WO 9808815 | 3/1998 |
| WO | WO 9808822 | 3/1998 |
| WO | WO 9808823 | 3/1998 |

(Continued)

OTHER PUBLICATIONS

Anonymous, "Enbrel® (etanercept)" 2004, [online]. Philadelphia, PA Wyeth Pharmaceuticals Inc., [retrieved on Nov. 26, 2004]. Retrieved from the Internet <http://www.enbrel.com/>.*

(Continued)

Primary Examiner—Thomas C. McKenzie

(57) ABSTRACT

Compounds of the formula

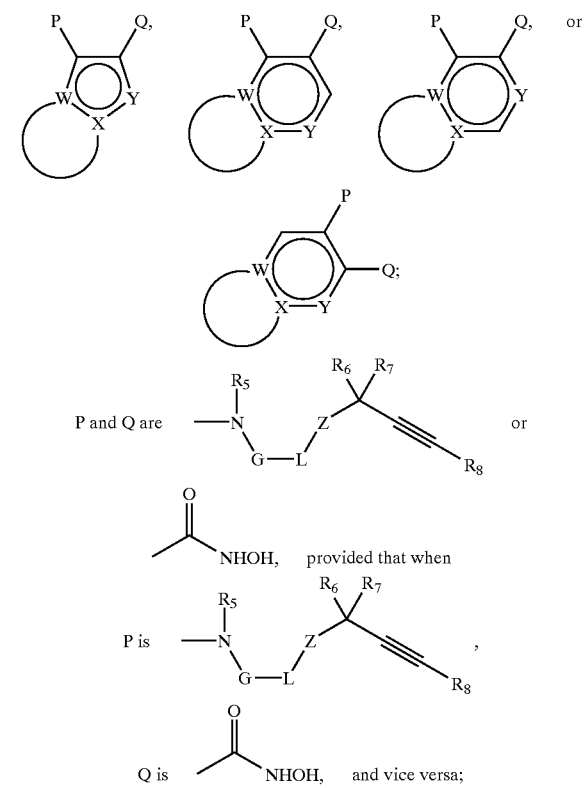

which are useful in disease conditions mediated by TNF-α, such as rheumatoid arthritis, osteoarthritis, sepsis, AIDS, ulcerative colitis, multiple sclerosis, Crohn's disease and degenerative cartilage loss.

14 Claims, No Drawings

FOREIGN PATENT DOCUMENTS

| | | |
|---|---|---|
| WO | WO 9808825 | 3/1998 |
| WO | WO 9808827 | 3/1998 |
| WO | WO 9808853 | 3/1998 |
| WO | WO 9816503 | 4/1998 |
| WO | WO 9816506 | 4/1998 |
| WO | WO 9816514 | 4/1998 |
| WO | WO 9816520 | 4/1998 |
| WO | WO 9833768 | 8/1998 |
| WO | WO 9834918 | 8/1998 |
| WO | WO 9837877 | 9/1998 |
| WO | WO 9839313 | 9/1998 |
| WO | WO 9839329 | 9/1998 |
| WO | WO 9842659 | 10/1998 |
| WO | WO 9843963 | 10/1998 |
| WO | WO 9925687 | 5/1999 |
| WO | WO 0044709 | 8/2000 |

OTHER PUBLICATIONS

Anonymous, "REMICADE® (infliximab)" Oct. 8, 2004, [online]. Centocor, Inc., [retrieved on Nov. 26, 2004]. Retrieved from the Internet <http://www.remicade.com/>.*

Roy A. Black, The International Journal of Biochemistry & Cell Biology vol. 34, Issue 1, Jan. 2002, pp. 1–5.*

Conway, J.G. et al, J Pharmacol Exp Ther. Sep. 2001;298(3):900–8.*

Beck, G. et al, J Pharmacol Exp Ther. Jul. 2002;302(1):390–6.*

Levin, J.I. et al, Bioorg Med Chem Lett. Aug. 18, 2003;13(16):2799–803.*

Shire, M.G., Exp. Opin. Ther. Patents 8(5), 531 (1998).
Grossman, J.M., Women's Health, 6(6), 627 (1997).
Isomaki, P.J., Ann. Med., 29, 499 (1997).
Camussi, G., Drugs, 55(5), 613 (1998).
Mathison et al., J. Clin. Invest., 81, 1925, (1988).
Miethke et al., J. Exp. Med., 175, 91 (1992).
Piquet, P. F., J. Exp. Med. 166, 1280 (1987).
Beuther, B., Ann. Rev., Biochem, 57, 505 (1988).
Ksontini, R., Arch, Surg., 133, 558, (1998).
Packer, M., Circulation, 92(6), 1379 (1995).
Ferrari, R., et al., Circulation 92(6), 1479 (1995).
Hotamisligil, G.S. et al., Science, 259, 87 (1993).
Peterson, P.K. et al., J. Clin. Invest., 89, 574 (1992).
Pallares–Trujillo et al., Med. Res. Reviews, 15(6), 533 (1995).
Old, L., Science, 230, 630 (1985).
Rankin, E.C. et al., Br. J. Rheumatol., 34, 334 (1995).
Pharmaprojects, Therapeutic Updates 17 (Oct.) au 197, M2Z (1996).
Mc Geehan et al., Current Pharmaceutical Design, 2, 662 (1996).
Script 20, 2349 (1998).
Mac Pherson et al., J. Med. Chem., 40, 2525 (1997).
Tamura et al., J. Med. Chem. 41, 640 (1998).
Pikul et al., J. Med. Chem., 41, 3568 (1998).

* cited by examiner

PREPARATION AND USE OF ACETYLENIC ORTHO-SULFONAMIDO AND PHOSPHINIC ACID AMIDO BICYCLIC HETEROARYL HYDROXAMIC ACIDS AS TACE INHIBITORS

This is a continuation of application(s) Ser. No. 09/492,978 filed on Jan. 27, 2000, now abandoned, the entire disclosure of which is hereby incorporated by reference, which claims the benefit of provisional application No. 60/198,221, filed Jan. 27, 1999.

FIELD OF INVENTION

This invention relates to acetylenic aryl or heteroaryl sulfonamide and phosphinic acid amide hydroxyamic acids which act as inhibitors of TNF-α converting enzyme (TACE). The compounds of the present invention are useful in disease conditions mediated by TNF-α, such as rheumatoid arthritis, osteoarthritis, sepsis, AIDS, ulcerative colitis, multiple sclerosis, Crohn's disease and degenerative cartilage loss.

BACKGROUND OF THE INVENTION

TNF-α converting enzyme (TACE) catalyzes the formation of TNF-α from membrane bound TNF-α precursor protein. TNF-α is a pro-inflammatory cytokine that is believed to have a role in rheumatoid arthritis [Shire, M. G.; Muller, G. W. *Exp. Opin. Ther. Patents* 1998, 8(5), 531; Grossman, J. M.; Brahn, E. *J. Women's Health* 1997, 6(6), 627; Isomaki, P.; Punnonen, *J. Ann. Med.* 1997, 29, 499; Camussi, G.; Lupia, E. *Drugs,* 1998, 55(5), 613.] septic shock [Mathison, et. al. *J. Clin. Invest.* 1988, 81, 1925; Miethke, et. al. *J. Exp. Med.* 1992, 175, 91.], graft rejection [Piguet, P. F.; Grau, G. E.; et. al. *J. Exp. Med.* 1987, 166, 1280.], cachexia [Beutler, B.; Cerami, A. *Ann. Rev. Biochem.* 1988, 57, 505.], anorexia, inflammation [Ksontini, R,; MacKay, S. L. D.; Moldawer, L. L. *Arch. Surg.* 1998, 133, 558.], congestive heart failure [Packer, M. *Circulation,* 1995, 92(6), 1379; Ferrari, R.; Bachetti, T.; et. al. *Circulation,* 1995, 92(6), 1479.], post-ischaemic reperfusion injury, inflammatory disease of the central nervous system, inflammatory bowel disease, insulin resistance [Hotamisligil, G. S.; Shargill, N. S.; Spiegelman, B. M.; et. al. *Science,* 1993, 259, 87.] and HIV infection [Peterson, P. K.; Gekker, G.; et. al. *J. Clin. Invest.* 1992, 89, 574; Pallares-Trujillo, J.; Lopez-Soriano, F. J. Argiles, J. M. *Med. Res. Reviews,* 1995, 15(6), 533.]], in addition to its well-documented antitumor properties [Old, L. *Science,* 1985, 230, 630.]. For example, research with anti-TNF-α antibodies and transgenic animals has demonstrated that blocking the formation of TNF-α inhibits the progression of arthritis [Rankin, E. C.; Choy, E. H.; Kassimos, D.; Kingsley, G. H.; Sopwith, A. M.; Isenberg, D. A.; Panayi, G. S. *Br. J. Rheumatol.* 1995, 34, 334; *Pharmaprojects,* 1996, Therapeutic Updates 17 (Oct.), au197-M2Z.]. This observation has recently been extended to humans as well as described in "TNF-α in Human Diseases", *Current Pharmaceutical Design,* 1996, 2, 662.

It is expected that small molecule inhibitors of TACE would have the potential for treating a variety of disease states. Although a variety of TACE inhibitors are known, many of these molecules are peptidic and peptide-like which suffer from bioavailability and pharmacokinetic problems. In addition, many of these molecules are non-selective, being potent inhibitors of matrix metalloproteinases and, in particular, MMP-1. Inhibition of MMP-1 (collagenase 1) has been postulated to cause joint pain in clinical trials of MMP inhibitors [*Scrip,* 1998, 2349, 20]. Long acting, selective, orally bioavailable non-peptide inhibitors of TACE would thus be highly desirable for the treatment of the disease states discussed above.

Examples of sulfonamide hydroxamic acid MMP/TACE inhibitors in which a 2 carbon chain separates the hydroxamic acid and the sulfonamide nitrogen, as shown below, are disclosed in WIPO international publications WO9816503, WO9816506, WO9816514 and WO9816520 and U.S. Pat. No. 5,776,961.

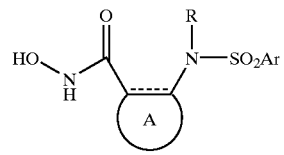

U.S. Pat. Nos. 5,455,258, 5,506,242, 5,552,419, 5,770,624, 5,804,593 and 5,817,822 as well as European patent application EP606,046A1 and WIPO international publications WO9600214 and WO9722587 disclose non-peptide inhibitors of matrix metalloproteinases and/or TACE of which the aryl sulfonamide hydroxamic acid shown below, in which 1 carbon separates the hydroxamic acid and the sulfonamide nitrogen, is representative. Additional publications disclosing sulfonamide based MMP inhibitors which are variants of the sulfonamide-hydroxamate shown below, or the analogous sulfonamide-carboxylates, are European patent applications EP-757037-A1 and EP-757984-A1 and WIPO international publications WO9535275, WO9535276, WO9627583, WO9719068, WO09727174, WO9745402, WO9807697, and WO9831664, WO9833768, WO9839313, WO9839329, WO9842659 and WO9843963. The discovery of this type of MMP inhibitor is further detailed by MacPherson, et. al. in *J. Med. Chem.,* (1997), 40, 2525 and Tamura, et. al. in *J. Med. Chem.* (1998), 41, 640.

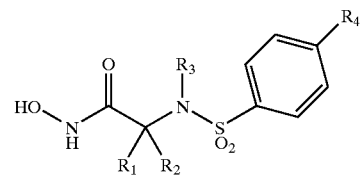

Publications disclosing β-sulfonamide-hydroxamate inhibitors of MMPs and/or TACE in which the carbon alpha to the hydroxamic acid has been joined in a ring to the sulfonamide nitrogen, as shown below, include U.S. Pat. No. 5,753,653, WIPO international publications WO9633172, WO9720824, WO9827069, WO9808815, WO9808822, WO9808823, WO9808825, WO9834918, WO9808827, Levin, et. al. *Bioorg. & Med. Chem. Letters* 1998, 8, 2657 and Pikul, et. al. *J. Med. Chem.* 1998, 41, 3568.

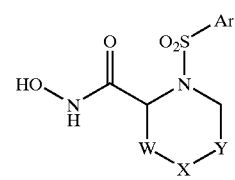

The patent applications DE19,542,189-A1, WO9718194, and EP803505 disclose additional examples of cylic sulfonamides as MMP and/or TACE inhibitors. In this case the sulfonamide-containing ring is fused to an aromatic or heteroaromatic ring.

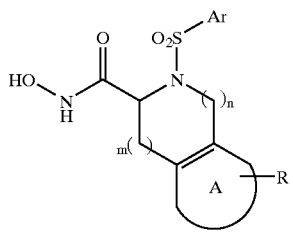

Analogous to the sulfonamides are the phosphinic acid amide hydroxamic acid MMP/TACE inhibitors, exemplified by the structure below, which have been disclosed in WIPO international publication WO9808853.

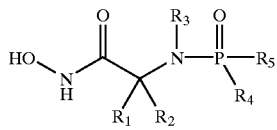

Sulfonamide MMP/TACE inhibitors in which a thiol is the zinc chelating group, as shown below, have been disclosed in WIPO international application 9803166.

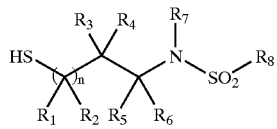

It is an object of this invention to disclose aryl or heteroaryl sulfonamide and phosphinic acid amide hydroxamic acid MMP/TACE inhibitors in which the L group is para-substituted with a substituted butynyl moiety or a propargylic ether, amine or sulfide. These compounds provide enhanced levels of inhibition of the activity of TACE in vitro and in a cellular assay and/or selectivty over MMP-1. These compounds may therefore be used in the treatment of diseases mediated by TNF.

DETAILED DESCRIPTION OF THE INVENTION

This invention provides TACE and MMP inhibitors having the formula:

B wherein B is

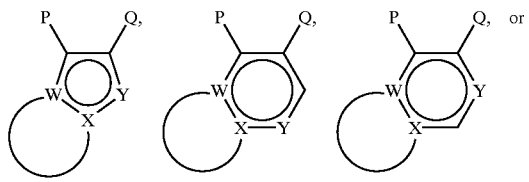

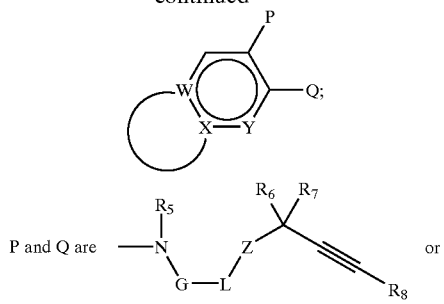

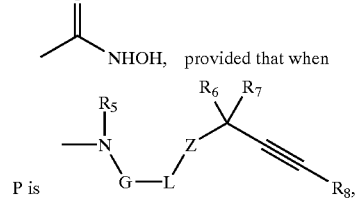

W and X are each, independently, carbon or nitrogen;
Y is carbon, nitrogen, oxygen or sulfur, provided that at least one of W, X, and Y is not carbon;
G is $SO_2$ or $-P(O)R_{10}$;
L is a phenyl, naphthyl or heteroaryl, with the proviso that G and Z may not be bonded to adjacent atoms of L,
Z is O, NH, S or $CH_2$;

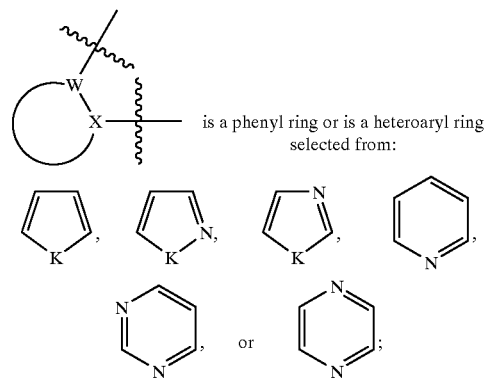

wherein K is O, $NR_9$ or S;
R5 is hydrogen or alkyl of 1–6 carbon atoms,
R6 and R7 are, independently, hydrogen, alkyl of 1–6 carbon atoms, —CN or —CCH;
R8 is hydrogen, alkyl of 1–6 carbon atoms, alkenyl of 2–6 carbon atoms, alkynyl of 2–6 carbon atoms, cycloalkyl of 3–6 carbon atoms, phenyl, naphthyl, or 5 to 10 membered heteroaryl having from 1–3 heteroatoms selected from N, NR9, O and S or 5–10 membered heterocycloalkyl having 1 or 2 heteroatoms selected from N, NR9, O and S;
R9 is hydrogen, alkyl of 1–6 carbon atoms, cycloalkyl of 3–6 carbon atoms, or phenyl; or a pharmaceutically acceptable salt thereof; and
R10 is phenyl, naphthyl, alkyl of 1–6 carbon atoms, cycloalkyl of 3–6 carbon atoms, heteroaryl, or 5–7 membered heterocycloalkyl ring; or a pharmaceutically acceptable salt thereof.

Preferred compounds of the present invention are provided wherein

B is

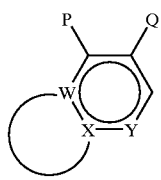

or a pharmaceutically acceptable salt thereof.
Still more preferred are compounds wherein:
B is

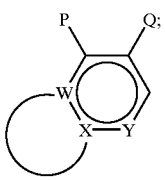

W and X are carbon;
Y is nitrogen;
or a pharmaceutically acceptable salt thereof.
Still more preferred are compounds wherein:
B is

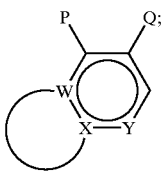

W and X are carbon;
Y is nitrogen;

P is ![structure with R5, N, G-L, Z, R6, R7, R8] and Q is ![C(=O)NHOH];

![ring structure with W, X]

is a phenyl, pyrazole, isoxazole or isothiazole:

or a pharmaceutically acceptable salt thereof.

In still more preferred embodiments of the present invention

B is

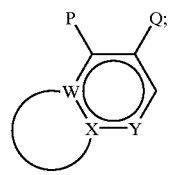

W and X are carbon;
Y is nitrogen;

P is ![structure with R5, N, G-L, Z, R6, R7, R8] and Q is ![C(=O)NHOH];

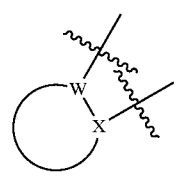

is a phenyl, pyrazole, isoxazole or isothiazole:
wherein L is a phenyl ring substituted at the 1- and 4-positions by G and Z, respectively;
or a pharmaceutically acceptable salt thereof.

In still more preferred embodiments of the present invention
B is

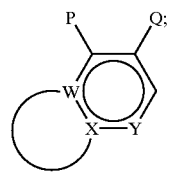

W and X are carbon;
Y is nitrogen;

P is ![structure with R5, N, G-L, Z, R6, R7, R8] and Q is ![C(=O)NHOH];

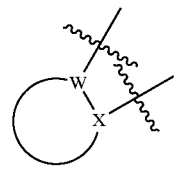

is a phenyl, pyrazole, isoxazole or isothiazole:
wherein L is a phenyl ring substituted at the 1- and 4-positions by G and Z, respectively; and G is $SO_2$;
or a pharmaceutically acceptable salt thereof.

In further embodiments of the present invention

B is

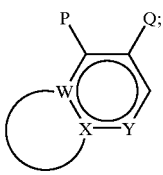

W and X are carbon;
Y is nitrogen;

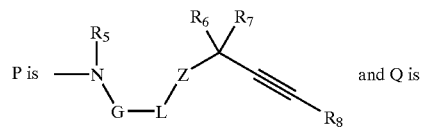

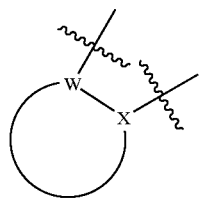

is a phenyl, pyrazole, isoxazole or isothiazole:
wherein L is a phenyl ring substituted at the 1- and 4-positions by G and Z, respectively; and G is SO$_2$; and Z is oxygen;
or a pharmaceutically acceptable salt thereof.

Further preferred embodiments of the present invention are provided where
B is

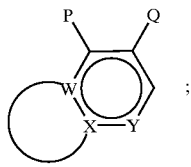

W and X are carbon;
Y is nitrogen;

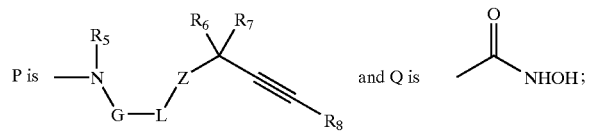

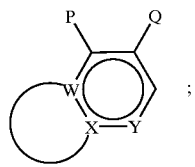

is a phenyl, pyrazole, isoxazole or isothiazole:
wherein L is a phenyl ring substituted at the 1- and 4-positions by G and Z, respectively; and G is SO$_2$; and Z is oxygen; and R$_6$ and R$_7$ are hydrogen;
or a pharmaceutically acceptable salt thereof.

In still more preferred embodiments
B is

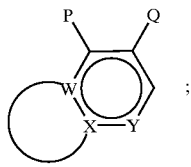

W and X are carbon;
Y is nitrogen;

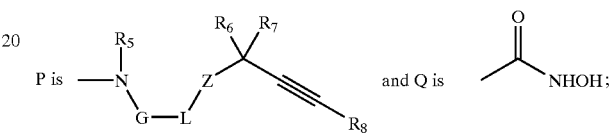

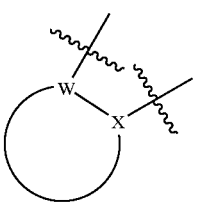

is a phenyl, pyrazole, isoxazole or isothiazole:
wherein L is a phenyl ring substituted at the 1- and 4-positions by G and Z, respectively; and G is SO$_2$; and Z is oxygen; and R$_6$ and R$_7$ are hydrogen; and R$_8$ is —CH$_2$OH or methyl;
or a pharmaceutically acceptable salt thereof.

Most preferred compounds of the present invention are:
4-[(4-But-2-ynyloxy-benzenesulfonyl)-methyl-amino]-1,3-dimethyl-1H-pyrazolo[3,4-b]pyridine-5-carboxylic acid hydroxyamide;
4-[(4-But-2-ynyloxy-benzenesulfonyl)-methyl-amino]-3-methyl-isoxazolo[5,4-b]pyridine-5-carboxylic acid hydroxyamide;
4-[(4-But-2-ynyloxy-benzenesulfonyl)-methyl-amino]-8-methoxy-quinoline-3-carboxylic acid hydroxyamide;
4-[(4-But-2-ynyloxy-benzenesulfonyl)-methyl-amino]-3-methyl-isothiazolo[5,4-b]pyridine-5-carboxylic acid hydroxyamide; and
8-Bromo-4-[{[4-(2-butynyloxy)phenyl]sulfonyl}(methyl)amino]-N-hydroxy-3-quinolinecarboxamide.

Heteroaryl, as used throughout, is a 5–10 membered mono- or bicyclic ring having from 1–3 heteroatoms selected from N, NR9, S and O. Heteroaryl is preferably

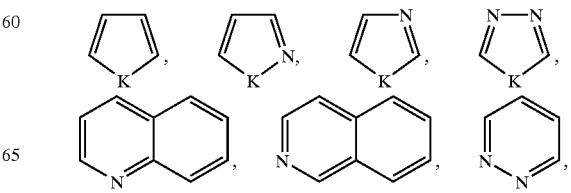

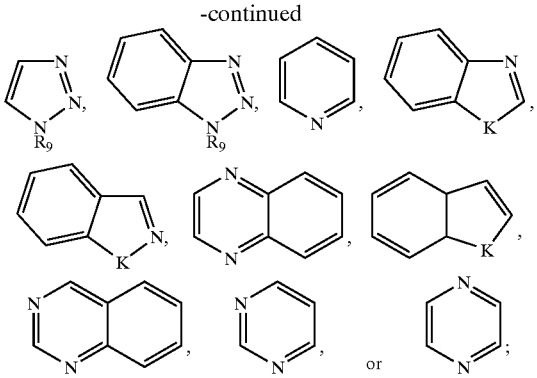

wherein K is NR9, O or S and R9 is hydrogen, phenyl, naphthyl, alkyl of 1–6 carbon atoms, or cycloalkyl of 3–6 carbon atoms. Preferred heteroaryl rings include pyrrole, furan, thiophene, pyridine, pyrimidine, pyridazine, pyrazine, triazole, pyrazole, imidazole, isothiazole, thiazole, isoxazole, oxazole, indole, isoindole, benzofuran, benzothiophene, quinoline, isoquinoline, quinoxaline, quinazoline, benzotriazole, indazole, benzimidazole, benzothiazole, benzisoxazole, and benzoxazole.

For purposes of the definition of A, It is still more preferred that A is a heteroaryl selected from

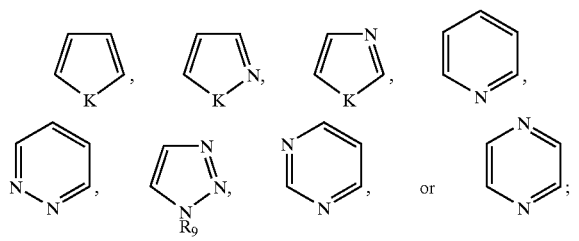

Heteroaryl groups of the present invention may optionally be mono- or di-substituted.

Heterocycloalkyl as used herein refers to a 5 to 10 membered saturated or unsaturated mono or bi-cyclic ring having 1 or 2 heteroatoms selected from N, NR9, S or O. Heterocycloalkyl rings of the present invention are preferably selected from

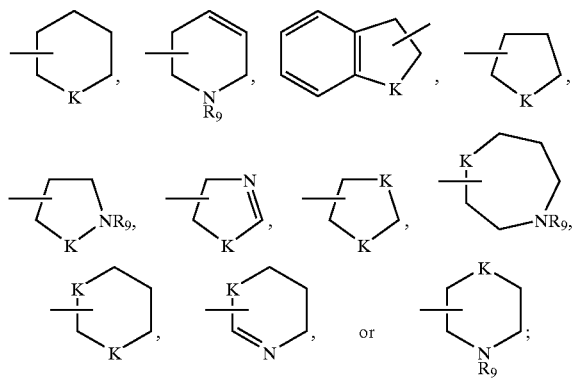

wherein K is NR9, O or S and R9 is hydrogen, phenyl, naphthyl, alkyl of 1–6 carbon atoms, or cycloalkyl of 3–6 carbon atoms. Preferred heterocycloalkyl rings include piperidine, piperazine, morpholine, tetrahydropyran, tetrahydrofuran or pyrrolidine. Heterocycloalkyl groups of the present invention may optionally be mono- or di-substituted.

Aryl, as used herein refers to phenyl or naphthyl which may, optionally be mono-, di- or tri-substituted.

Alkyl, alkenyl, alkynyl, and perfluoroalkyl include both straight chain as well as branched moieties. Alkyl, alkenyl, alkynyl, and cycloalkyl groups may be unsubstituted (carbons bonded to hydrogen, or other carbons in the chain or ring) or may be mono- or poly-substituted.

Halogen means bromine, chlorine, fluorine, and iodine.

Suitable substituents of aryl, heteroaryl, alkyl, alkenyl, alkynyl, cycloalkyl and include, but are not limited to halogen, alkyl of 1–6 carbon atoms, alkenyl of 2–6 carbon atoms, alkynyl of 2–6 carbon atoms, cyclocalkyl of 3–6 carbon atoms, —$OR_2$, —CN, —$COR_2$, perfluoroalkyl of 1–4 carbon atoms, —O-perfluoroalkyl of 1–4 carbon atoms, —$CONR_2R_3$, —$S(O)_nR_2$—$OPO(OR_2)OR_3$, —$PO(OR_2)R_3$, —$OC(O)NR_2R_3$, —$C(O)NR_2OR_3$, —$COOR_2$, —$SO_3H$, —$NR_2R_3$, —$N[(CH_2)_2]_2NR_2$, —$NR_2COR_3$, —$NR_2COOR_3$, —$SO_2NR_2R_3$, —$NO_2$, —$N(R_2)SO_2R_3$, —$NR_2CONR_2R_3$, —$NR_2C(=NR_3)NR_2R_3$, —$NR_2C(=NR_3)N(SO_2R_2)R_3$, $NR_2C(=NR_3)N(C=OR_2)R_3$, —$SO_2NHCOR_4$, —$CONHSO_2R_4$, -tetrazol-5-yl, —$SO_2NHCN$, —$SO_2NHCONR_2R_3$, phenyl, naphthyl, heteroaryl or heterocycloalkyl;

wherein —$NR_2R_3$ may form a pyrrolidine, piperidine, morpholine, thiomorpholine, oxazolidine, thiazolidine, pyrazolidine, piperazine, or azetidine ring;

$R_2$ and $R_3$ are each, independently, hydrogen, alkyl of 1–6 carbon atoms, cycloalkyl of 3–6 carbon atoms, phenyl, naphthyl, heteroaryl or heterocycloalkyl;

$R_4$ is alkyl of 1–6 carbon atoms, alkenyl of 2–6 carbon atoms, alkynyl of 2–6 carbon atoms, cycloalkyl of 3–6 carbon atoms; perfluoroalkyl of 1–4 carbon atoms, phenyl, naphthyl, heteroaryl or heterocycloalkyl, and n is 0–2.

Suitable substituents of heterocycloalkyl groups of the present invention include, but are not limited to alkyl of 1–6 carbon atoms, cycloalkyl of 3–6 carbon atoms, phenyl, naphthyl, heteroaryl and heterocycloalkyl.

When a moiety contains more than substituent with the same designation each of those substituents may be the same or different.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains an acidic moiety.

The compounds of this invention may contain an asymmetric carbon atom and some of the compounds of this invention may contain one or more asymmetric centers and may thus give rise to optical isomers and diastereomers. While shown without respect to stereochemistry, the present invention includes such optical isomers and diastereomers; as well as the racemic and resolved, enantiomerically pure R and S stereoisomers; as well as other mixtures of the R and S stercoisomers and pharmaceutically acceptable salts thereof. It is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

The compounds of this invention are shown to inhibit the enzymes MMP-1, MMP-9, MMP-13 and TNF-α converting enzyme (TACE) and are therefore useful in the treatment of arthritis, tumor metastasis, tissue ulceration, abnormal wound healing, periodontal disease, graft rejection, insulin resistance, bone disease and HIV infection. In particular, the compounds of the invention provide enhanced levels of inhibition of the activity of TACE in vitro and in cellular assay and/or enhanced selectivity over MMP-1 and are thus particularly useful in the treatment of diseases mediated by TNF.

The invention is further directed to a process for making compounds of structure B involving one or more reactions as follows:

1) alkylating a compound of formula I, or a salt or solvate thereof,

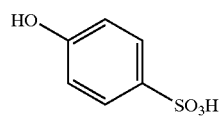

I into a compound of formula II

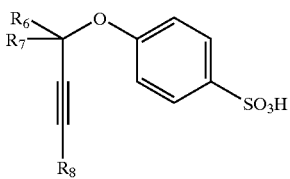

II 2) reacting a compound of formula II above, or a salt or solvate thereof, with a chlorinating agent such as thionyl chloride, chlorosulfonic acid, oxalyl chloride, phosphorus pentachloride, or other halogenating agents such as fluorosulfonic acid or thionyl bromide to a compound of formula III:

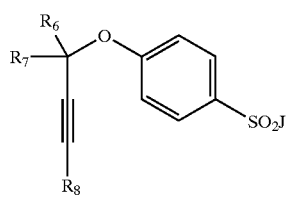

III wherein J is fluorine, bromine, chlorine.

The resultant sulfonyl chloride, fluoride or bromide, may be further converted into triazolide, imidazolide or benzothiazolide derivatives, where J is 1,2,4-triazolyl, imidazolyl or benzotriazolyl, by reacting the compound with 1,2,4-triazole, imidazole or benzotriazole, respectively. $R_6$, $R_7$, and $R_8$ are as defined above.

The invention is still further directed to a process for making compounds of structure B involving one or more reactions as follows:

1) alkylating phenol, or a salt or solvate thereof, into a compound of formula IV:

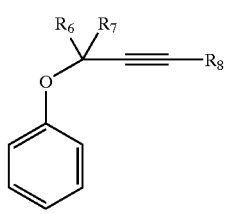

IV 2) reacting a compound of formula IV above, or a salt or solvate thereof with chlorosulfonic acid to prepare a compound of formula II above.

Particularly preferred intermediates are compounds of formulae II and III, with the proviso that R8 is not hydrogen.

The compounds of this invention can be prepared according to the following schemes from commercially available starting materials or starting materials which can be prepared using to literature procedures. Typical known starting materials are shown below (V–XXV). These schemes, which follow thereafter, show the preparation of representative compounds of this invention.

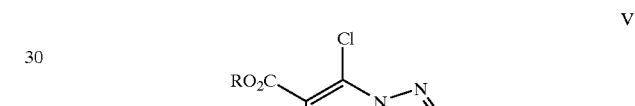

V

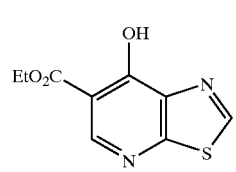

VI

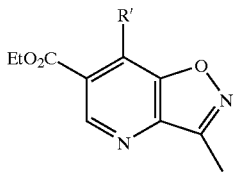

VII

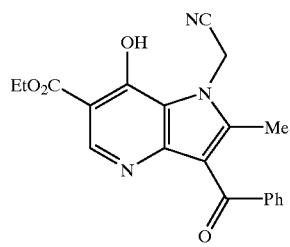

VIII

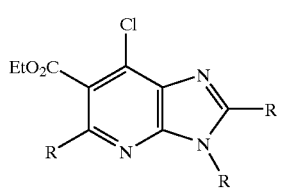

IX

-continued
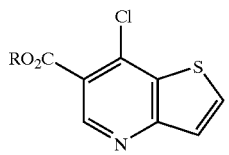 X
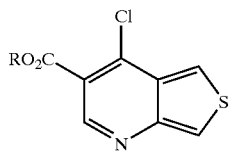 XI
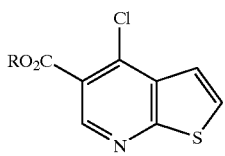 XII
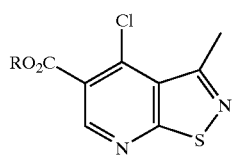 XIII
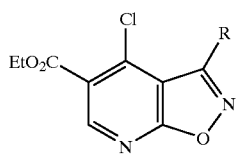 XIV
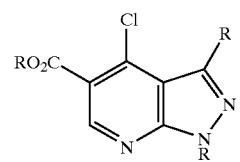 XV
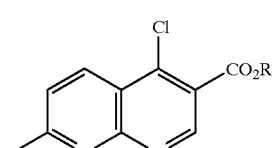 XVI
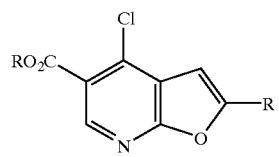 XVII
-continued
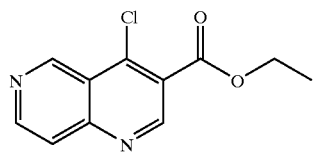 XVIII
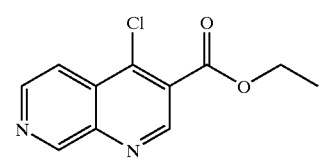 XIX
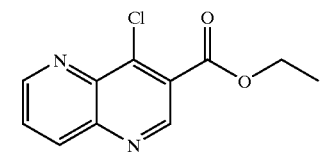 XX
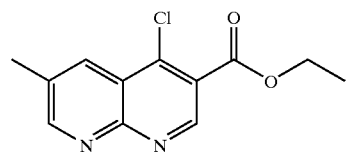 XXI
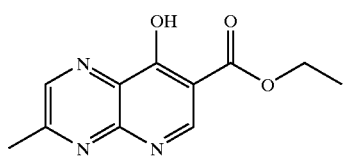 XXII
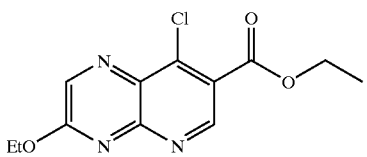 XXIII
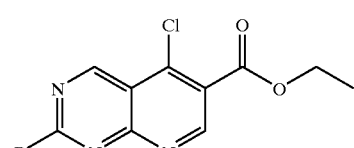 XXIV
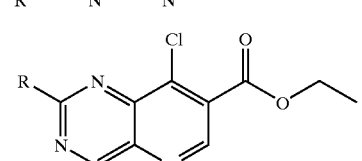 XXV
Compound V:
a) Springer, R H; Scholten, M B; O'Brien, D E, Novinson, T; Miller, J P; Robins, R K *J. Med. Chem.* 1982, 25(3), 235–42.
b) Elworthy, T. R.; Ford, A. P. D.; et. al. *J. Med. Chem.* 1997, 40(17), 2674–2687.

Compound VI:
Masui, T; TAkura, T; JP 46043792; JP 690307; CAN 76:59604
Compound VII:
Camparini, A; Ponticelli, F; Tedeschi, P *J. Chem. Soc., Perkin Trans.*1 1982, 10, 2391–4.
Compound VIII:
Abdalla, G M; Sowell. J W *J. Heterocycl. Chem.* 1990, 27(5), 1201–7.
Compound IX:
a) Denzel, T; Hoehn, H *J. Heterocyclic Chem.* 1977, 14, 813–817.
b) Al-Shaar, A H M; Chambers, R K; Gilmour, D W; Lythgoe, D J; McClenaghan, I; Ramsden, C A *J. Chem. Soc.; Perkin Trans. I* 1992, 21, 2789–2812.
c) Elworthy, T. R.; Ford, A. P. D.; et. al. *J. Med. Chem.* 1997, 40(17), 2674–2687.
Compound X:
a) Forbes, I T; Johnson, C N; Jones, G E; Loudon, J; Nicholass, J M *J. Med. Chem* 1990, 2640–2645.
b) Kan, M A; Guarconi, A E *J. Heterocyclic Chem* 1977, 14, 807–812.
Compound XI:
a) Forbes, I T; Johnson, C N; Jones, G E; Loudon, J; Nicholass, J M *J. Med. Chem* 1990, 2640–2645.
b) Kan, M A; Guarconi, A E *J. Heterocyclic Chem* 1977, 14, 807–812.
Compound XII:
a) Richardson, T O; Neale, N; Carwell, N *J. Heterocyclic. Chem.* 1995, 32, 359–361.
b) Baker, J M; Huddleston, P R; Keenan, G J *J. Chem Research Miniprint,* 1982, 6, 1726–1746.
Compound XIII:
a) Forbes, I T; Johnson, C N; Jones, G E; Loudon, J; Nicholass, J M *J. Med. Chem* 1990, 2640–2645.
b) Kan, M A; Guarconi, A E *J. Heterocyclic Chem* 1977, 14, 807–812.
Compounds XIV, XV and XVI:
Elworthy, T. R.; Ford, A. P. D.; et. al. *J. Med. Chem.* 1997, 40(17), 2674–2687.
Compound XVII:
*Heterocycles* 1997, 45, 980.
Compound XVIII:
Yokoyama, Naokata. Eur. Pat. Appl., 61 pp. CODEN: EPXXDW. EP 115469 A1 840808.
Compound XIX:
Mendes, Etienne; Vernieres, Jean Claude; Simiand, Jacques Edouard; Keane, Peter Eugene. Eur. Pat. Appl., 12 pp. CODEN: EPXXDW. EP 346207 A1 891213.
Compound XX:
Mendes, Etienne; Vernieres, Jean Claude; Simiand, Jacques Edouard; Keane, Peter Eugene. Eur. Pat. Appl., 12 pp. CODEN: EPXXDW. EP 346207 A1 891213.
Compound XXI:
Morita, Yoshiharu; Wagatsuma, Kazuo. Japan. Kokai, 4 pp. CODEN: JKXXAF. JP 50058094 750520 Showa.
Compounds XXII and XXIII:
Armitage, Bernard John; Leslie, Bruce William; Miller, Thomas Kerr; Morley, Christopher. PCT Int. Appl., 110 pp. CODEN: PIXXD2. WO 9500511 A1 950105.
Compound XXIV:
Minami, S.; Matsumoto, J.; Kawaguchi, K.; Mishio, S.; Shimizu, M.; Takase, Y.; Nakamura, S. (Dainippon Pharmaceutical Co., Ltd., Japan) Japan. Kokai, 3pp. CODEN: JKXXAF. JP 50014697 750215 Showa.
Compound XXV:
Kihara, N.; Tan, H.; Takei, M.; Ishihara, T. (Mitsui Pechochemical Industries, Ltd., Japan; Suntory, Ltd.) Jpn.
Kokai Tokyo Koho, 11pp. CODEN: JKXXAF. JP 62221686 A2 870929 Showa.

The compounds of this invention can be prepared using conventional techniques known to those skilled in the art of organic synthesis. The following schemes (Schemes 1–11) illustrate the reaction sequences employed. In the schemes which follow, the moiety A is defined as the bicyclic heteroaryl moiety of B, as shown immediately below:

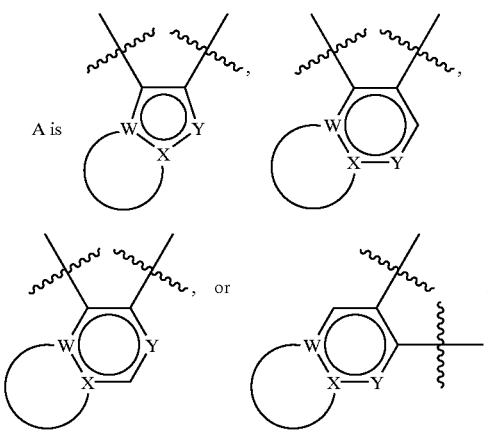

Those skilled in the art will recognize that certain reactions are best carried out when other potentially reactive functionality on the molecule is masked or protected, thus avoiding undesirable side reactions and/or increasing the yield of the reaction. To this end, those skilled in the art may use protecting groups. Examples of these protecting group moieties may be found in T. W. Greene, P. G. M. Wuts *"Protective Groups in Organic Synthesis"*, $2^{nd}$ Edition, 1991, Wiley & Sons, New York. Reactive side chain functionalities on amino acid starting materials are preferably protected. The need and choice of protecting groups for a particular reaction is known to those skilled in the art and depends on the nature of the functional group to be protected (hydroxy, amino, carboxy, etc.), the structure and stability of the molecule of which the substituent is part and the reaction conditions.

When preparing or elaborating compounds of the invention containing heterocyclic rings, those skilled in the art recognize that substituents on that ring may be prepared before, after or concomitant with construction of the ring. Those skilled in the art will recognize that the nature and order of the synthetic steps presented may be varied for the purpose of optimizing the formation of the compounds of the invention.

The hydroxamic acid compounds of the invention, 1, are prepared according to Scheme 1 by converting a carboxylic acid, 2, into the corresponding acid chloride or anhydride, or by reacting it with a suitable peptide coupling reagent such a 1-[3-(dimethylamino)propyl]-3-ethylcarbodiimide hydrochloride (EDC) and 1-hydroxy-benzotriazole hydrate (HOBT), followed by reaction with hydroxylamine to give 1, or with a protected hydroxylamine derivative to give 3. Compounds 3, wherein $R_{30}$ is a t-butyl, benzyl, trialkylsilyl or other suitable masking group may then be deprotected by known methods to provide the hydroxamic acid 1.

Scheme 1

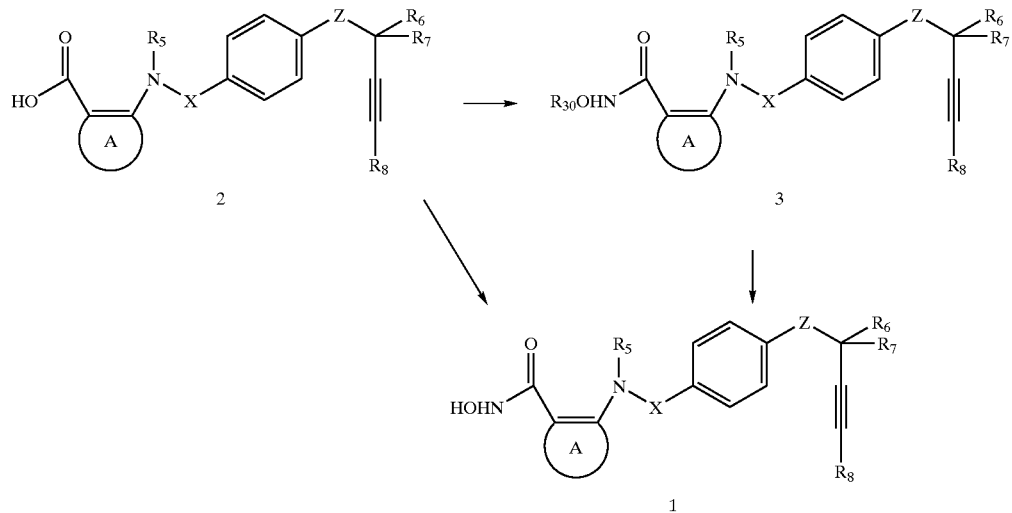

Carboxylic acids 2 may be prepared as shown in Scheme 2 wherein X is G as herein before defined. Chloro-ester 4, in which $R_{40}$ is hydrogen or a suitable carboxylic acid protecting group, may be reacted with sulfonamides 5, to provide the ortho-sulfonamido-ester 6. Hydrolysis of the ester is performed by acid, base hydrolysis, or other method consistent with the choice of protecting group $R_{40}$ to provide carboxylic acid 2. Alternatively, chloro-ester 4 first reacts with a primary amine to provide 7 which is then sulfonylated or phosphorylated with 8, in which J is a suitable leaving group including but not limited to chlorine, to give ester 6.

Scheme 2

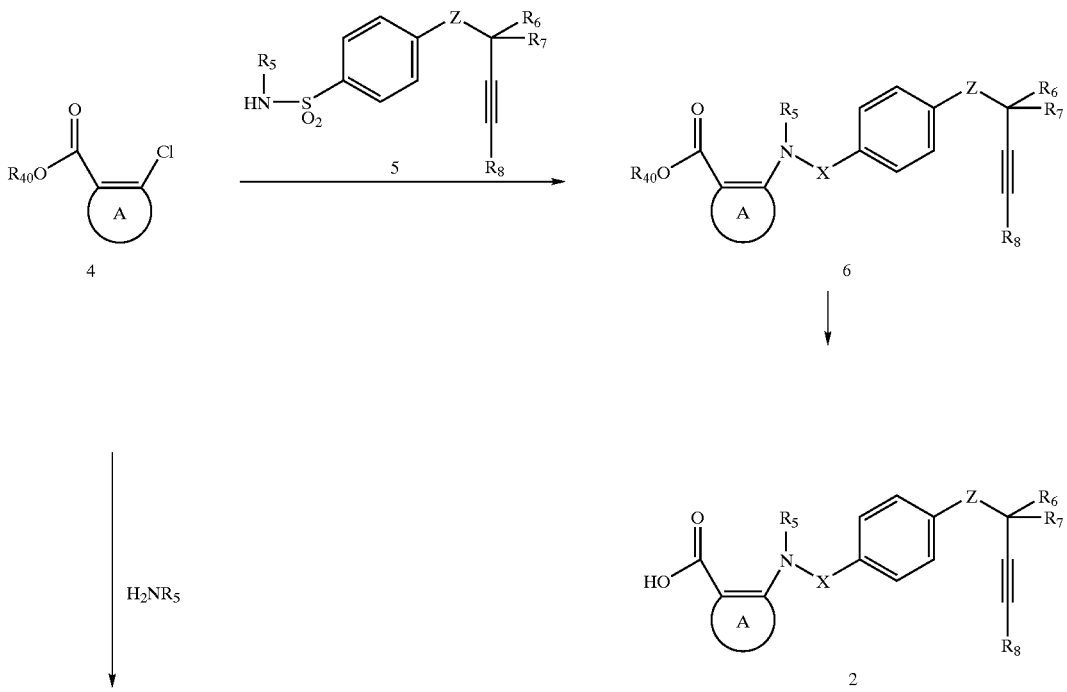

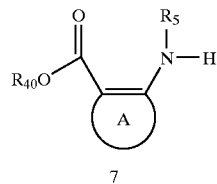

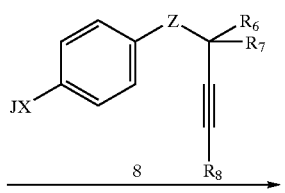

Methods of preparation of sulfonylating agents 8 and sulfonamides 5 are shown in Scheme 3. Thus, sulfonic acid salts 9, where $ZR_{50}$ is a hydroxy, thiol or substituted amino moiety may be alkylated with acetylenes 10, where J is a suitable leaving group such as halogen mesylate, tosylate, or triflate to give 11. Acetylenes 10 are commercially available or known compounds, or they may be synthesized by known methods by those skilled in the art. The sulfonic acid salts 11 may be converted into the corresponding sulfonyl chloride or other sulfonylating agent 8 by known methods, such as reaction with oxalyl chloride or other reagent compatible with substituents $R_6$, $R_7$ and $R_8$ and the acetylene. Alternatively, the disulfide 12 may be converted into di-acetylene 13 by reaction with compounds 10, followed by reduction of the disulfide bond to provide the analogous thiols which may be converted into 8 by known methods. Alkylation of the phenol, thiophenol, aniline or protected aniline 14 with 10 to give 15, followed by reaction, with chlorosulfonic acid provide sulfonic acids 16 which are readily converted into 8 with oxalyl chloride or similar reagents. Thiophenols 17 are also precursors to 8 via protection of the thiol, alkylation of ZH, where Z is O, N or S, and deprotection of the sulfur followed by oxidation to the sulfonic acid 16. Sulfonamides 5 are prepared from 8 by reaction with primary amines $R_5NH_2$. The phosphorylating agents 8, wherein X is $P(O)R_4$, are prepared from 15 using standard methodology.

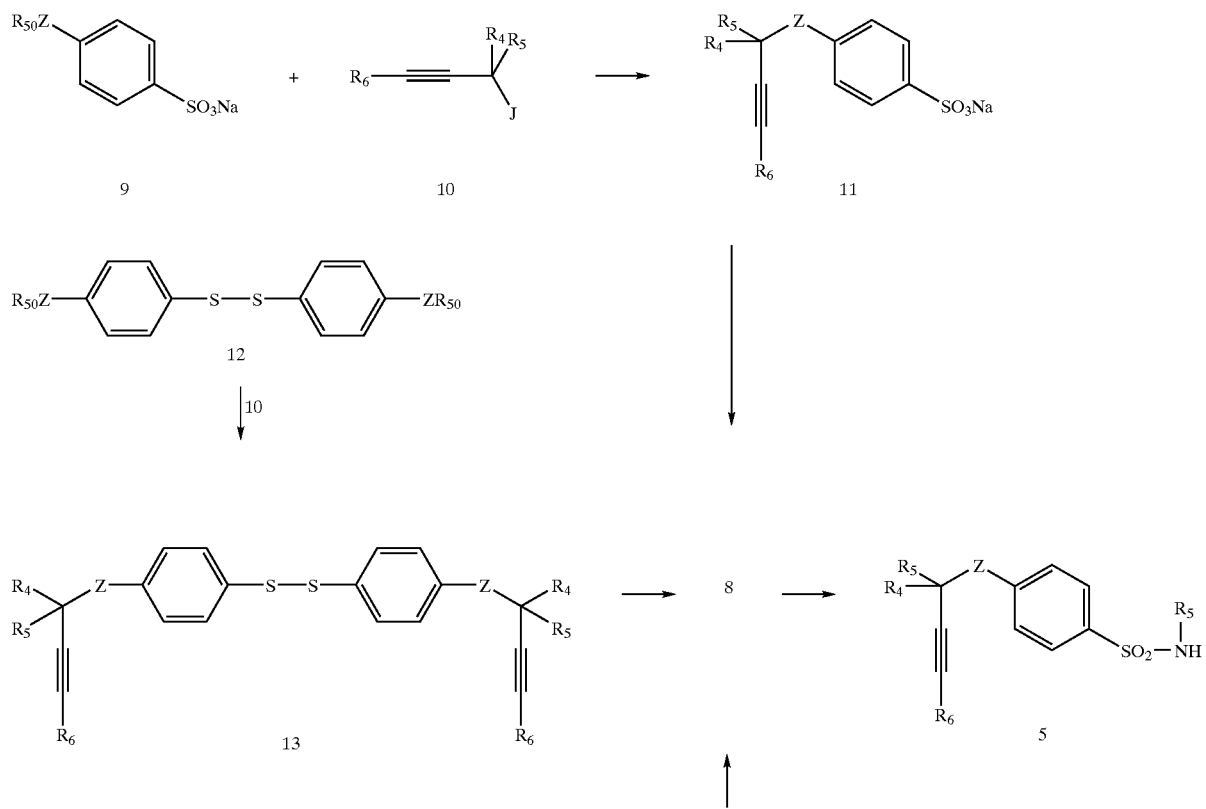

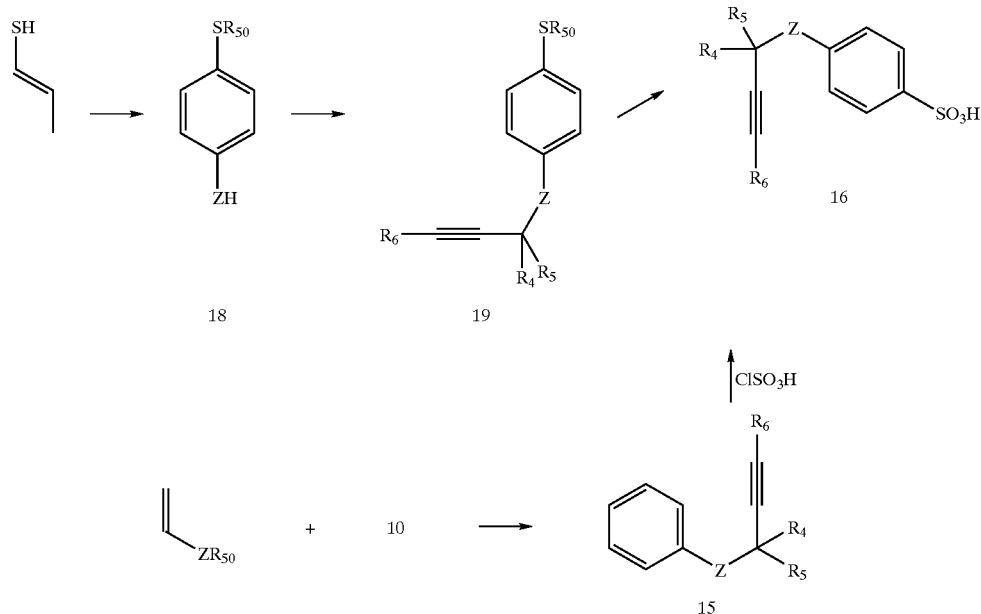

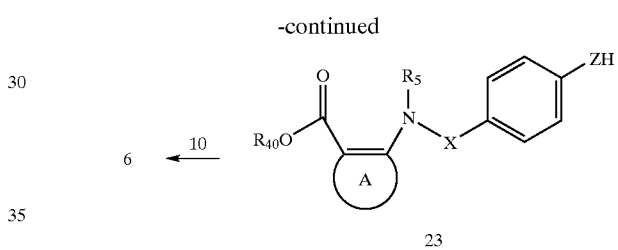

The acetylenic side chain may also be appended after chloride displacement from 4 or functionalization of 7, as shown in Scheme 4. Thus, chloro-ester 4 can react with compounds 20, where $ZR_{50}$ is hydroxy or protected hydroxy, thiol or amine, to give 21. Removal of the $R_{50}$ masking group to give 23 and subsequent alkylation of the resulting phenol, thiol or amine with 10 provides 6. In the case where $ZR_{50}$ is equal to OH, no deprotection step is required to give 23. Compound 21 can also be formed from amino-ester 7 and 22.

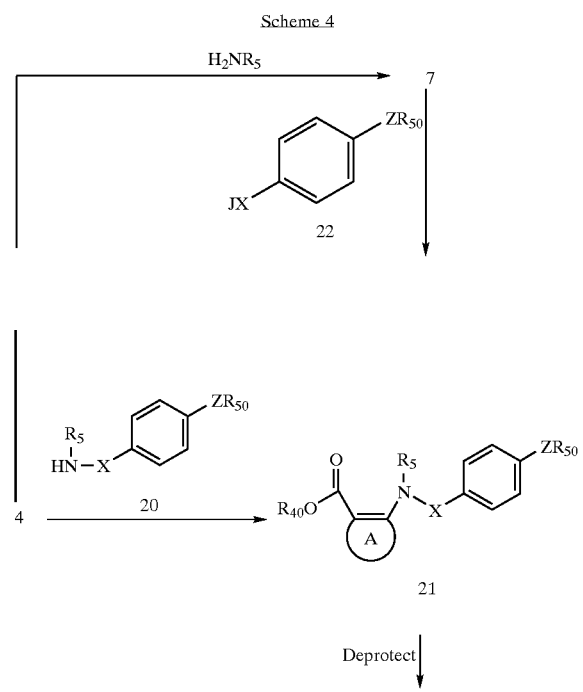

Acetylenic derivatives 6 are also accessible via the fluoro compounds 26, readily prepared from 4 and/or 7 by reaction with fluoraryl 24, as shown in Scheme 5. Displacement of the fluorine of 26 in the presence of a base such as sodium hydride with a masked hydroxy, thiol, or amino group ($HZR_{70}$, where R70 is a suitable protecting group) in a polar aprotic solvent such as DMF, followed by deprotection gives 23, which can then be alkylated with 10 to provide 6. Conversion of 26 to 23, where Z is sulfur, might also be accomplished with $Na_2$, $K_2S$, NaSH or KS(C=S)OEt. The fluorine of 26 can also be displaced in a polar aprotic solvent with the propargylic derivative 27, where Z is O, S or NH, in the presence of a base such as sodium hydride, to give 6 directly.

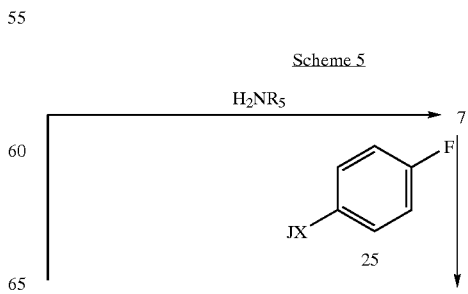

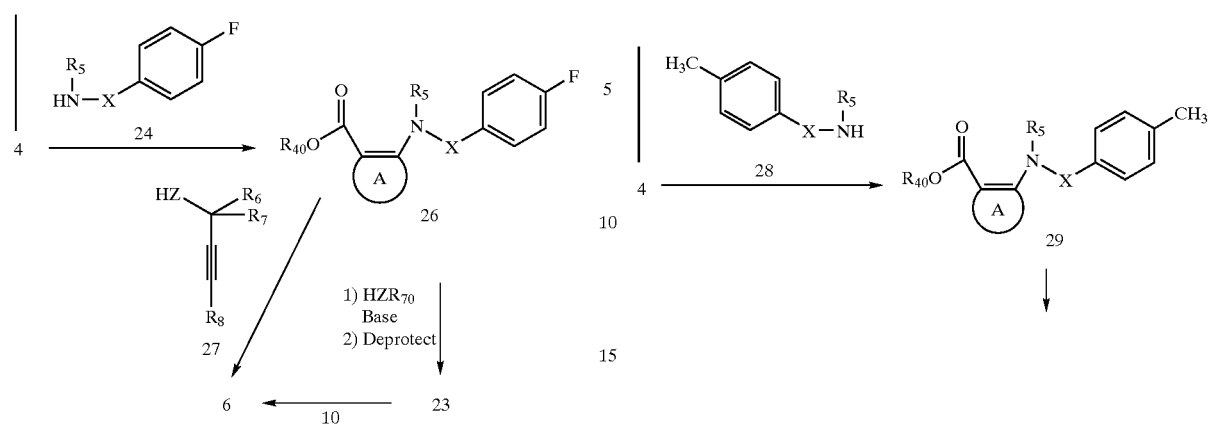

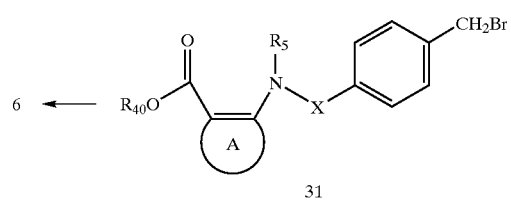

Compound 6, wherein Z is a methylene group, is available via 29, as shown in Scheme 6. Benzylic bromination of 29 with N-bromosuccinimide in a chlorinated hydrocarbon solvent provides bromide 31. This is followed by displacement of the bromide with the appropriate propynyl cuprate to provide sulfonamide 6.

Scheme 6

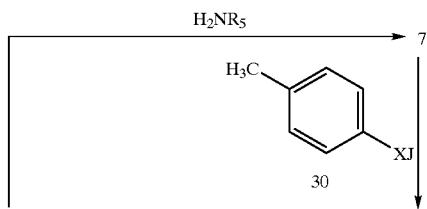

The propargylic amine analogs of 6 can be synthesized as shown in Scheme 7 starting from 4 and/or 7. Reduction of the nitro moiety of 34 with hydrogen and palladium on carbon, tin chloride or other known method to give aniline 35 and subsequent alkylation with 10 then provides 6. Aniline 35 may be derivatized to form 36 prior to alkylation with 10, and then deprotected after the alkylation step.

Scheme 7

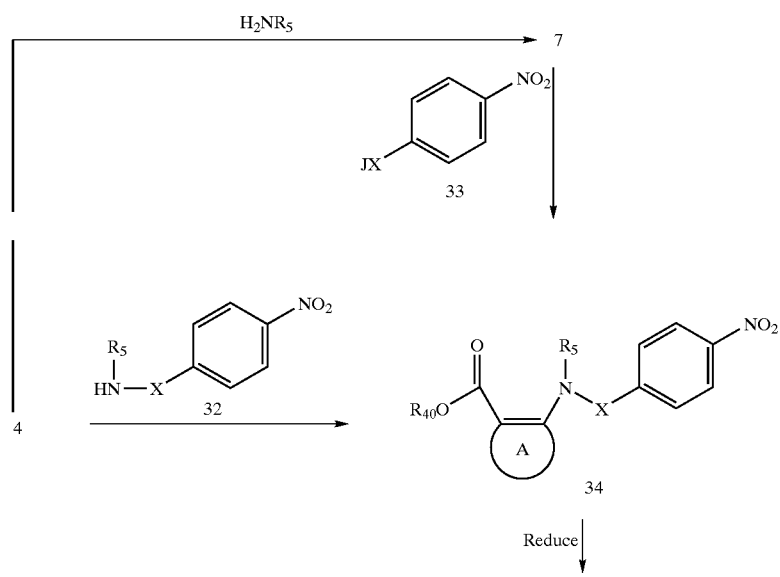

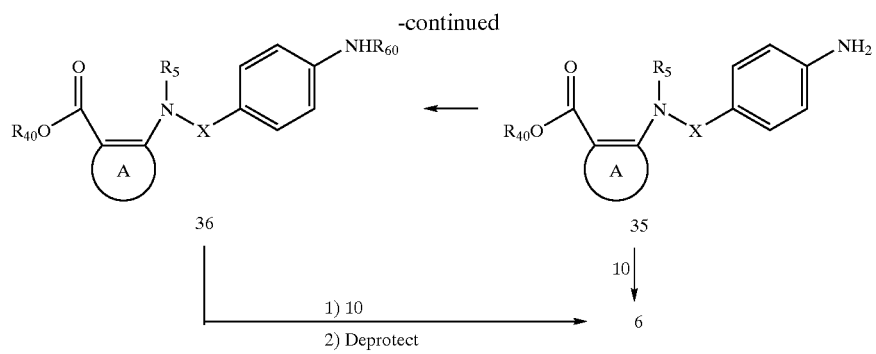

Compounds of the invention can also be prepared by modifying substituents on the acetylenic side chain at any stage after formation of esters 6. Functional groups such as halogen, hydroxy, amino, aldehyde, ester, ketone, etc. may be manipulated by standard methods to form the moieties defined by $R_1$, $R_2$, $R_5$ and $R_8$ of compounds 1. It is recognized by those skilled in the art of organic synthesis that the successful use of these methods is dependent upon the compatibility of substituents on other parts of the molecule. Protecting groups and/or changes in the order of steps described herein may be required.

Some of the methods available for the derivatization of compounds of structure 37 (equivalent to compound 6 wherein $R_8$ is hydrogen) are shown in Scheme 8. Metallation of the terminal acetylene 37 followed by addition of an aldehyde or alkyl halide, sulfonate or triflate provides derivatives 38 and 39. Reaction of 37 with formaldehyde and an amine provides the Mannich addition product 40. Cyanogen bromide addition to 40 gives the propargylic bromide 41 which may be displaced with a variety of nucleophiles to give, for example, ethers, thioethers and amines. Palladium catalyzed coupling reactions of 37 provide the aryl or heteroaryl acetylenes 43. It is recognized by those skilled in the art of organic synthesis that the successful use of these methods is dependent upon the compatibility of substituents on other parts of the molecule. Protecting groups and/or changes in the order of steps described herein may be required.

Scheme 8

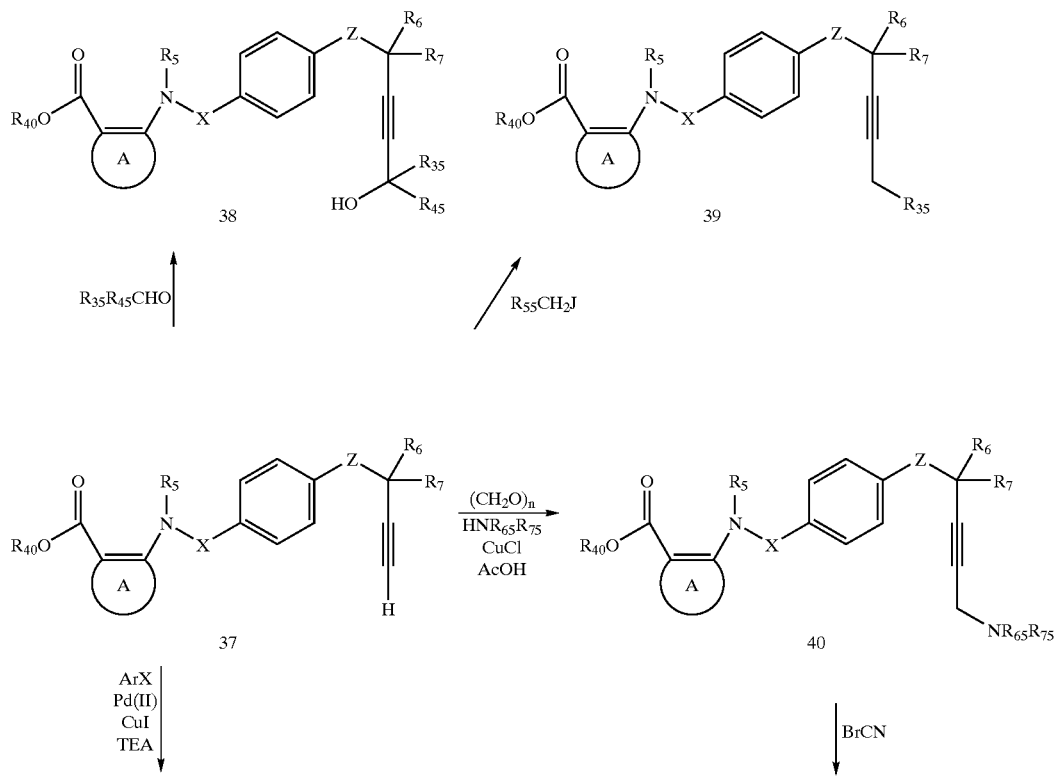

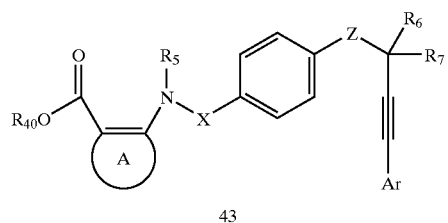

43

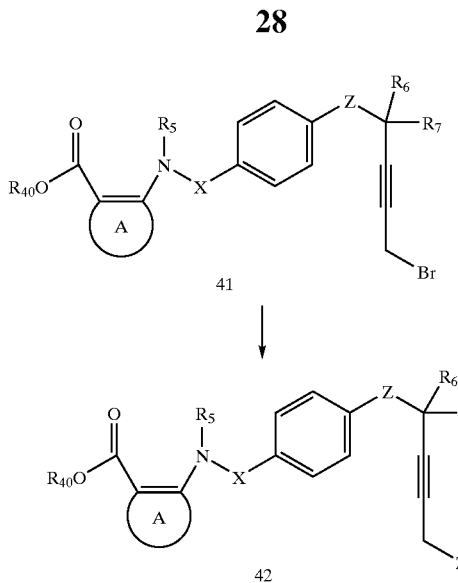

41

42

For purposes of illustration only, methods of preparation for the bicyclic heteroaryl chloro-esters 4 used as a starting material in Schemes 2 and 4–7, wherein A is a quinoline, pyrazolopyridine, isoxazolopyridine, isothiazolopyridine and pyrazolo[1,5-b]pyrimidine, are shown in Schemes 9–11. The quinolines are prepared as shown in Scheme 9 starting from the corresponding aniline and an alkoxymethylenemalonate, such as diethyl ethoxymethylenemalonate. The resulting hydroxy-ester can be converted into the desired chloroester 4 via reaction with phosphorus oxychloride.

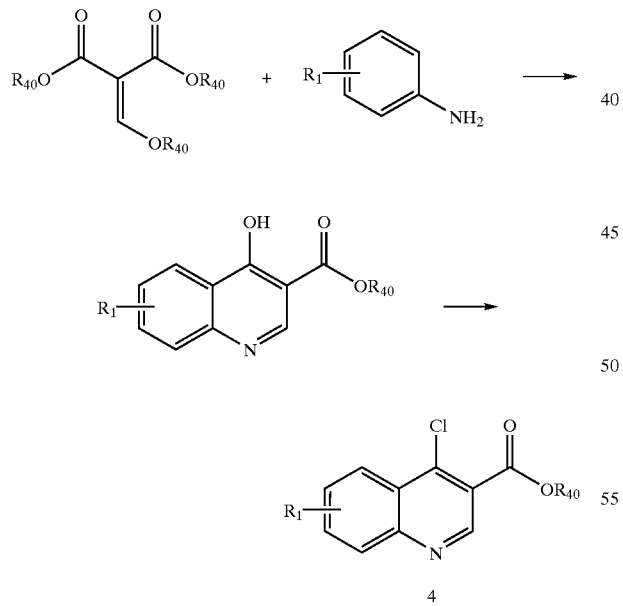

Scheme 10 illustrates the synthesis of pyrazolopyridines, isoxazolopyridines, and isothiazolopyridines of the invention. Thus, an aminopyrazole, aminoisoxazole or aminoisothiazole is condensed with an alkoxymethylenemalonate to provide the intermediate aminomethylenemalonate. This compound is cyclized into the pyrazolopyridine, isoxazolopyridine, or isothiazolopyridine by heating at 240° C. in diphenyl ether. The resulting bicyclic heteroaryl hydroxy-ester is then converted into the chloro-ester via reaction with phosphorus oxychloride.

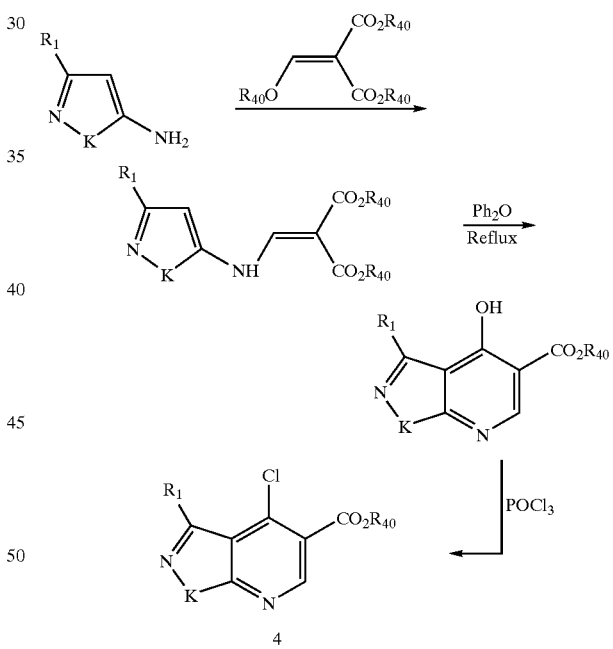

Pyrazolo[1,5-b]pyrimidines of the invention are prepared according to Scheme 11 using reactions as described for Scheme 10.

Scheme 11

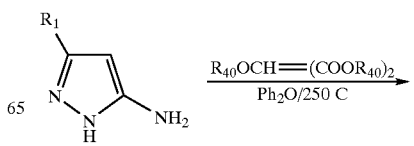

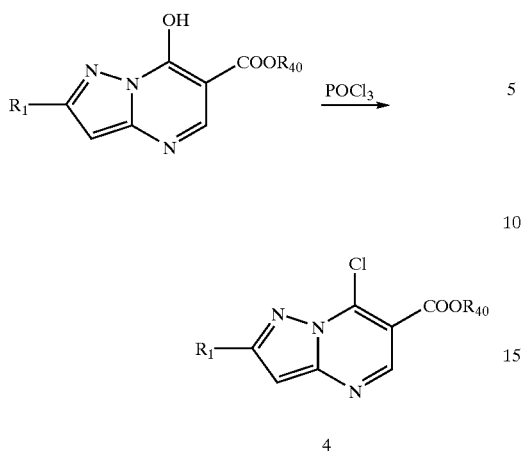

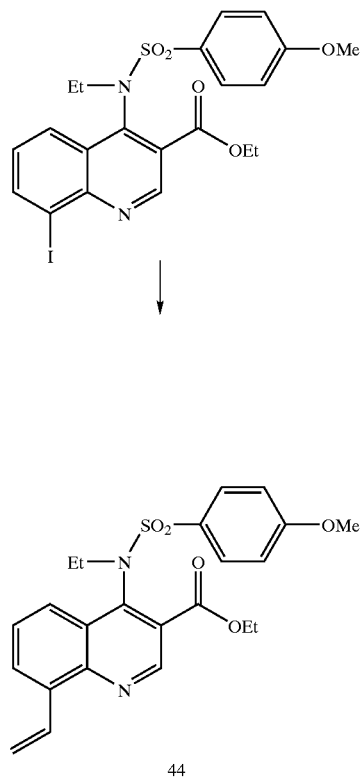

Functionalization of the bicyclic heteroaryl ring A is shown in Scheme 12 wherein, for illustration purposes only, A is a quinoline ring. The iodoquinoline and tributylvinyltin react via a palladium catalyzed Heck coupling. α,β-Unsaturated esters and amides can also be coupled to the haloquinoline via Heck reactions. A variety of other trialkyltin reagents are readily available and may be similarly used. Boronic acids, commercially available or readily prepared, may also be coupled to the iodoquinoline using the Suzuki reaction. Compounds such as 44 can be converted into the compounds of the invention according to Schemes 4, 2 and 1 using boron tribromide or other suitable deprotecting agent to cleave the methyl ether.

Scheme 12

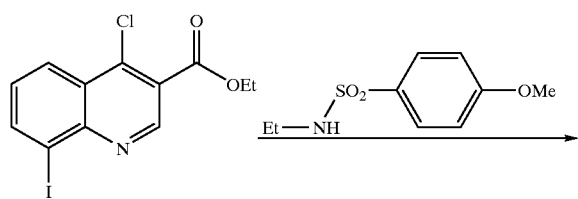

Functionalization of haloheteroaryls may also be accomplished via palladium catalyzed couplings of alkynes, as illustrated in Scheme 13 for a quinoline ring. Hydrogenation of the alkynes accesses the olefins and alkanes as well. Compounds 45 and 46 can be converted into the compounds of the invention according to Schemes 4, 2 and 1 using boron tribromide or other suitable deprotecting agent to cleave the methyl ether.

Scheme 13

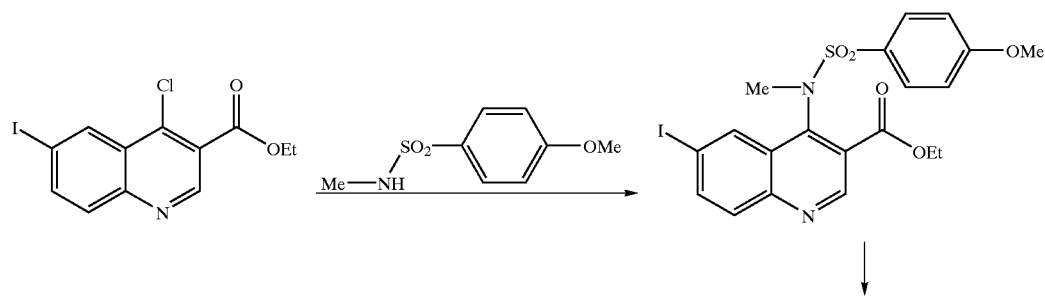

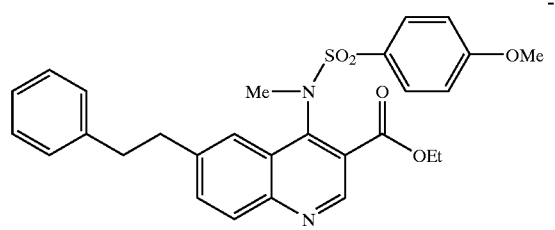

46

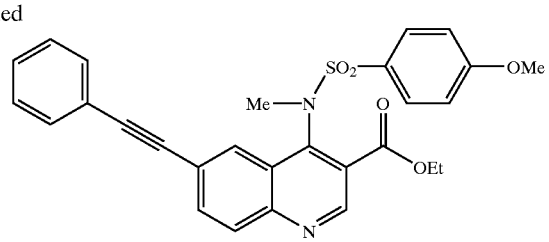

45

Scheme 14 illustrates a method for incorporating amino groups into the substituent attached to the sulfonamide nitrogen of the compounds of the invention. Thus, in Scheme 14 the NH-sulfonamide is alkylated with propargyl bromide to provide the propargyl sulfonamide. This alkyne is reacted with paraformaldehyde in the presence of a primary or secondary amine and cuprous chloride to give the propargyl amine 47 which is converted into the compounds of the invention according to Schemes 1 and 2.

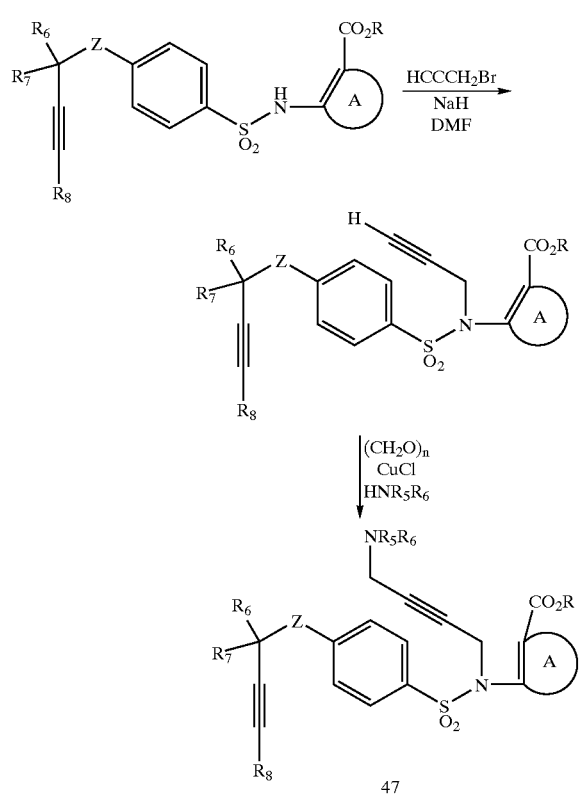

The following specific examples illustrate the preparation of representative compounds of this invention. The starting materials, intermediates, and reagents are either commercially available or can be readily prepared following standard literature procedures by one skilled in the art of organic synthesis.

EXAMPLE 1

4-But-2-ynyloxy-benzenesulfonic acid sodium salt

To a solution of 52.35 g (0.225 mol) of 4-hydroxybenzenesulfonate sodium salt in 1 L of isopropanol and 225 mL of a 1.0N solution of sodium hydroxide was added 59.96 g (0.45 mol) of 1-bromo-2-butyne. The resulting mixture was heated to 70° for 15 h and then the isopropanol was removed by evaporation in vacuo. The resulting white precipitate was collected by filtration, washed with isopropanol and ether and dried in vacuo to give 56.0 g (100%) of the butynyl ether as a white solid.

EXAMPLE 2

4-But-2-ynyloxy-benzenesulfonyl chloride

To a 0° solution of 43.8 mL (0.087 mol) of 2M oxalyl chloride/dichloromethane solution in 29 mL of dichloromethane was dropwise added 6.77 mL (0.087 mol) of DMF followed by 7.24 g (0.029 mol) of the product of Example 1. The reaction mixture was stirred for 10 minutes at 0° then let warm to room temperature and stirred for 2 days. The reaction was then poured into ice and extracted with 150 mL of hexanes. The organics were washed with water and brine, dried over $Na_2SO_4$, filtered and concentrated in vacuo to provide 6.23 g (88%) of the sulfonyl chloride as a yellow solid; m.p. 63–65° C. EI Mass Spec: 243.9 ($M^+$).

EXAMPLE 3

But-2-ynyloxy-benzene

To a solution of 6.14 g (0.023 mol) of triphenylphosphine dissolved in 100 mL of benzene and 40 mL of THF was added 1.75 mL (0.023 mol) of 2-butyn-1-ol. After five minutes 2.00 (0.023 mol) phenol, dissolved in 10 mL of THF, was added to the reaction followed by 3.69 mL (0.023 mol) of diethyl azodicarboxylate. The resulting reaction mixture was stirred for 18 h at room temperature and then concentrated in vacuo. The residue was chromatographed on silica gel eluting with ethyl acetate/hexanes (1:10) to provide 2.18 g (70%) of the butynyl ether as a clear liquid.

EI Mass Spec: 146.0 $MH^+$.

EXAMPLE 4

4-But-2-ynyloxy-benzenesulfonyl chloride

To a solution of 0.146 g (1.0 mmol) of the product of Example 3 in 0.3 mL of dichloromethane in an acetone/ice bath under $N_2$ was dropwise added a solution of 0.073 mL (1.1 mmol) of chlorosulfonic acid in 0.3 mL of dichloromethane. After the addition was complete, the ice bath was removed and the reaction was stirred at room temperature for 2 h. To the reaction was then dropwise added 0.113 mL (1.3 mmol) of oxalyl chloride, followed by 0.015 mL DMF. The reaction was heated to reflux for 2 h and then diluted with hexane and poured into ice water. The organic layer was washed with brine, dried over sodium sulfate, and concentrated in vacuo to provide 0.130 mg (53%) of the desired product as a light brown solid.

EXAMPLE 5

4-But-2-ynyloxy-N-methyl-benzenesulfonamide

To 22.5 mL (0.045 mol) of a 2M solution of methylamine in dichloromethane, cooled to 0° C., was added a solution of 3.67 g (0.015 mol) of 4-but-2-ynyloxy-benzenesulfonyl chloride in 45 mL of dichloromethane. The reaction was allowed to warm to room temperature and stirred for 48 h. The resulting solution was poured into water and extracted with dichloromethane. The combined organics were washed with 2N citric acid solution, water and brine, dried over $Na_2SO_4$, filtered through Magnesol® and concentrated in vacuo to provide 3.23 g (92%) of the N-methyl sulfonamide as a white solid; m.p.78–80° C.

Anal. For $C_{11}H_{13}NO_3S$; Calc: C, 55.21; H, 5.88; N, 5.85. Found: C, 55.49; H, 5.65; N, 5.80.

EXAMPLE 6

4-[(4-But-2-ynyloxy-benzenesulfonyl)-methyl-amino]-1,3-dimethyl-1H-pyrazolo[3,4-b]pyridine-5-carboxylic acid ethyl ester To solution of 1.196 g (5.00 mmol) of the product of Example 5 in 40 mL of 1-methyl-2-pyrrolidinone was added 3.45 g (0.025 mol) of potassium carbonate 1.268 g (5.00 mmol) of ethyl-4-chloro-5,7-dimethylpyrazole[3,4-b]pyridine-3-carboxylate and 0.075 g of 18-crown-6 and the resulting mixture was heated to ~100° C. for 12 h. The reaction mixture was then concentrated in vacuo and the residue was diluted with ethyl acetate and water. The organics were washed with water, 2N citric acid solution and brine, dried over $Na_2SO_4$, passed through Magnesol® and concentrated in vacuo. The residue was chromatographed on silica gel eluting with ethyl acetate/hexanes (1:2) to provide 0.89 g (39%) of the product as a solid; m.p.50–52° C.

Anal. For $C_{22}H_{24}N_4O_5S$; Calc: C, 57.88; H, 5.30; N, 12.27. Found: C, 57.25; H, 5.34; N, 12.07.

EXAMPLE 7

4-[(4-But-2-ynyloxy-benzenesulfonyl)-methyl-amino]-1,3-dimethyl-1H-pyrazolo[3,4-b]pyridine-5-carboxylic acid and 4-[(4-But-2-ynyloxy-benzenesulfonyl)-methyl-amino]-1,3-dimethyl-1H-pyrazolo[3,4-b]pyridine-5-carboxylic acid hydroxyamide To a solution of 0.82 g (1.798 mmol) of the product of Example 6 in 10 mL of THF and 5 mL of methanol was added 2.15 mL of a 1N solution of sodium hydroxide and the resulting mixture was heated to reflux for 3 h and then concentrated in vacuo. The residue was triturated with ether and the solid was collected by filtration and dried in vacuo to provide 0.77 g (95%) of the carboxylate salt as a white solid.

To a 0° solution of 1.67 mL (3.34 mmol) of a 2.0M solution of oxalyl chloride in dichloromethane, diluted with 8.0 mL of dichloromethane, is added 0.258 mL (3.34 mmol) of DMF and the reaction is stirred for 15 minutes at 0°. A solution of 0.75 g (1.67 mmol) of the carboxylate salt, suspended in 5 mL of DMF, was added to the reaction and the resulting mixture is stirred for 1 h at room temperature and then poured into a 0° mixture of 1.395 mL of triethylamine, 3 mL of THF and 0.408 mL of a 50% aqueous solution of hydroxylamine. The reaction was allowed to warm to room temperature overnight and the organics are then concentrated in vacuo. The residue is diluted with dichloromethane and water, acidified with 2N citric acid solution, washed with water and brine, dried over $Na_2SO_4$, filtered and concentrated in vacuo. The residue was chromatographed on silica gel eluting with ethyl acetate/methanol (4:1) to provide 0.28 g (38%) of the hydroxamic acid as a white solid; m.p. 189–192° C.

Anal. For $C_{20}H_{21}N_5O_5S$; Calc: C, 54.17; H, 4.77; N, 15.79. Found: C, 54.14; H, 4.77; N, 15.43.

EXAMPLE 8

4-[(4-But-2-ynyloxy-benzenesulfonyl)-methyl-amino]-3-methyl-isoxazolo[5,4-b]pyridine-5-carboxylic acid ethyl ester To a suspension of 0.105 g (0.63 mmol) of 60% sodium hydride in 8 mL of 1-methyl-2-pyrrolidinone was added 0.628 g (2.63 mmol) of the product of Example 5 and the resulting mixture was stirred for 30 minutes at room temperature. A solution of 0.601 g (2.50 mmol) of ethyl-4-chloro-3-methylisoxazolo[5,4-b]pyridine-5-carboxylate in 7 mL of 1-methyl-2-pyrrolidinone was added and the reaction was heated to 80–90° C. for 48 h. The reaction mixture was then concentrated in vacuo and the residue was diluted with dichloromethane. The organics were washed with water, 2N citric acid solution and brine, dried over $Na_2SO_4$, filtered through Magnesol® and concentrated in vacuo. The residue was triturated with ethyl acetate/hexanes and the resulting solid was filtered and dried in vacuo to provide 1.0 g (90%) of the product as a solid; m.p.85–90° C. Electrospray Mass Spec: 444 (M+H)$^+$.

EXAMPLE 9

4-[(4-But-2-ynyloxy-benzenesulfonyl)-methyl-amino]-3-methyl-isoxazolo[5,4-b]pyridine-5-carboxylic acid and 4-[(4-But-2-ynyloxy-benzenesulfonyl)-methyl-amino]-3-methyl-isoxazolo[5,4-b]pyridine-5-carboxylic acid hydroxyamide According to the procedure of Example 7, the ethyl ester product of Example 8 was converted into the carboxylic acid (white solid, m.p.187–190° C.) and then into the hydroxamic acid (white solid, m.p.201–202° C.).

EXAMPLE 10

4-[(4-But-2-ynyloxy-benzenesulfonyl)-methyl-amino]-8-methoxy-quinoline-3-carboxylic acid ethyl ester According to the procedure of Example 6, 8-methoxy-4-chloro-quinoline-3-carboxylic acid ethyl ester reacted with 4-but-2-ynyloxy-N-methyl-benzenesulfonamide to provide the sulfonamido-quinoline as a white solid, m.p.131–132° C. Electrospray Mass Spec: 468.9 (M+H)$^+$

EXAMPLE 11

4-[(4-But-2-ynyloxy-benzenesulfonyl)-methyl-amino]-8-methoxy-quinoline-3-carboxylic acid and 4-[(4-But-2-ynyloxy-benzenesulfonyl)-methyl-amino]-8-methoxy-quinoline-3-carboxylic acid hydroxyamide According to the procedure of Example 7, the ethyl ester product of Example 10 was converted into the carboxylic acid (white solid, m.p.238° C., dec.; Electrospray Mass Spec: 440.9 (M+H)$^+$) and then into the hydroxamic acid (white solid, m.p.179–181° C.; Electrospray Mass Spec: 455.9 (M+H)$^+$).

EXAMPLE 12

4-[(4-But-2-ynyloxy-benzenesulfonyl)-methyl-amino]-3-methyl-isothiazolo[5,4-b]pyridine-5-carboxylic acid ethyl ester According to the procedure of Example 6, ethyl 4-chloro-3-methylisothiazolo[5,4-b]pyridine-5-carboxylate reacted with 4-but-2-ynyloxy-N-methyl-benzenesulfonamide to provide the sulfonamido-quinoline as a white solid, m.p.55–57° C. Electrospray Mass Spec: 460 (M+H)$^+$

EXAMPLE 13

4-[(4-But-2-ynyloxy-benzenesulfonyl)-methyl-amino]-3-methyl-isothiazolo[5,4-b]pyridine-5-carboxylic acid and 4-[(4-But-2-ynyloxy-benzenesulfonyl)-methyl-amino]-3-methyl-isothiazolo[5,4-b]pyridine-5-carboxylic acid hydroxyamide According to the procedure of Example 7, the ethyl ester product of Example 12 was converted into the carboxylic acid (white solid, m.p.230–232° C.; Electrospray Mass Spec: 431.8 (M+H)$^+$) and then into the hydroxamic acid (white solid, m.p.183–184° C.; Electrospray Mass Spec: 447 (M+H)$^+$).

EXAMPLE 14

4-[Benzyl-(4-methoxy-benzenesulfonyl)-amino]-7-trifluoromethyl-quinoline-3-carboxylic acid ethyl ester To a solution of 1.85 g (6.67 mmol) of N-benzyl 4-methoxyphenyl-sulphonamide in 15 mL of DMF was added, in one portion, 0.267 g (6.67 mmol) of 60% sodium hydride and the resulting mixture was stirred at room temperature under nitrogen for 15 min. Ethyl 4-chloro-7-trifluoromethyl-3-quinolinecarboxylate (2.02 g, 6.67 mmol) was then added to the solution in one portion and the resulting mixture was heated at 85° C. for 24 h. The reaction mixture was then cooled to room temperature, poured into a mixture of water (300 mL) and HCl (1N, aqueous, 100 mL) and extracted with ethyl acetate (2×100 mL). The combined organic layers were dried over magnesium sulfate, filtered and concentrated in vacuo. The residue was then chromatographed on silica gel eluting with 15%–50% ethyl acetate/hexane to give 3.11 g (88%) of the desired product. Electrospray Mass Spec 545.1 (M+H)$^+$.

EXAMPLE 15

4-[Benzyl-(4-methoxy-benzenesulfonyl)-amino]-8-trifluoromethyl-quinoline-3-carboxylic acid ethyl ester In the same manner as described in Example 14, 1.012 g (3.34 mmol) of ethyl 4-chloro-8-trifluoromethyl-3-quinolinecarboxylate provided 1.509 g (83%) of the desired quinoline ester as a white solid. Electrospray Mass Spec 545.1 (M+H)$^+$.

EXAMPLE 16

4-[Benzyl-(4-methoxy-benzenesulfonyl)-amino]-6-bromo-quinoline-3-carboxylic acid ethyl ester In the same manner as described in Example 14, 0.848 g (2.70 mmol) of ethyl 6-bromo-4-chloro-3-quinolinecarboxylate provided 1.418 g (95%) of the desired quinoline ester as a white solid. Electrospray Mass Spec 557.1 (M+H)$^+$.

EXAMPLE 17

4-[Benzyl-(4-methoxy-benzenesulfonyl)-amino]-7-bromo-quinoline-3-carboxylic acid ethyl ester In the same manner as described in Example 14, 0.777 g (2.47 mmol) of ethyl 7-bromo-4-chloro-3-quinolinecarboxylate provided 1.169 g (85%) of the desired quinoline ester as a white solid. Electrospray Mass Spec 557.1 (M+H)$^+$.

EXAMPLE 18

4-[Benzyl-(4-methoxy-benzenesulfonyl)-amino]-6-trifluoromethyl-quinoline-3-carboxylic acid ethyl ester In the same manner as described in Example 14, 1.216 g (4.02 mmol) of ethyl 4-chloro-6-trifluoromethyl-3-quinolinecarboxylate provided 2.171 g (99%) of the desired quinoline ester as a white solid. Electrospray Mass Spec 545.0 (M+H)$^+$.

EXAMPLE 19

4-[Benzyl-(4-methoxy-benzenesulfonyl)-amino]-7-trifluoromethyl-quinoline-3-carboxylic acid To a solution of 1.065 g (2.00 mmol) of the product from Example 14 in 4 mL of methanol/THF (1:1) was added 2 mL of 1N sodium hydroxide solution and the resulting mixture was stirred at 25° C. for 18 h. The reaction was then acidified with 1N HCl and extracted with ethyl acetate (200 mL). The organic layer was washed with water and brine, dried over MgSO$_4$, filtered and concentrated in vacuo. The resulting residue was triturated with ethyl acetate/hexane (1:9) and filtered to provide 828 mg (82%) of the desired carboxylic acid as a white solid. Electrospray Mass Spec 517.1 (M+H)$^+$

EXAMPLE 20

4-[Benzyl-(4-methoxy-benzenesulfonyl)-amino]-8-trifluoromethyl-quinoline-3-carboxylic acid In the same manner as described in Example 19, 1.255 g (2.64 mmol) of the product from Example 15 provided 0.988 g (83%) of the desired quinoline acid as a white solid. Electrospray Mass Spec 517.1 (M+H)$^+$.

EXAMPLE 21

4-[Benzyl-(4-methoxy-benzenesulfonyl)-amino]-6-bromo-quinoline-3-carboxylic acid In the same manner as described in Example 19, 1.198 g (2.16 mmol) of the product from Example 16 provided 0.921 g (81%) of the desired quinoline acid as a white solid. Electrospray Mass Spec 529.0 (M+H)$^+$.

EXAMPLE 22

4-[Benzyl-(4-methoxy-benzenesulfonyl)-amino]-7-bromo-quinoline-3-carboxylic acid In the same manner as described in Example 19, 0.969 g (1.74 mmol) of the product from Example 17 provided 0.804 g (87%) of the desired quinoline acid as a white solid. Electrospray Mass Spec 529.0 (M+H)$^+$.

EXAMPLE 23

4-[Benzyl-(4-methoxy-benzenesulfonyl)-amino]-6-trifluoromethyl-quinoline-3-carboxylic acid In the same manner as described in Example 19, 2.043 g (3.75 mmol) of the product from Example 18 provided 1.82 g (88%) of the desired quinoline acid as a white solid. Electrospray Mass Spec 515.0 $(M-H)^+$.

EXAMPLE 24

4-[Ethyl-(4-methoxy-benzenesulfonyl)-amino]-8-iodo-quinoline-3-carboxylic acid ethyl ester In the same manner as described in Example 14 and substituting N-ethyl-4-methoxybenzenesulfonamide for N-benzyl-4-methoxybenzenesulfonamide, 1.076 g (5.00 mmol) of ethyl 8-iodo-4-chloro-3-quinolinecarboxylate provided 2.438 g (4.51 mmol, 90%) of the desired quinoline ester as a white solid. Electrospray Mass Spec 541.0 $(M+H)^+$.

EXAMPLE 25

4-[Ethyl-(4-methoxy-benzenesulfonyl)-amino]-8-vinyl-quinoline-3-carboxylic acid ethyl ester The product from Example 24 (2.438 g, 4.51 mmol) in 150 mL DMF was added tributylvinyltin (1.43 g, 4.51 mmol), tetrakis(triphenylphosphine)palladium(0) (520 mg, 10%), cuprous iodide (171 mg, 20%), and 5 mL triethylamine. The mixture was stirred under $N_2$ and heated at 85° C. for 18 hours. The it was poured into a mixture (1:1) of 400 mL saturated sodium bicarbonate and saturated ammonium chloride and extracted with ethyl acetate (2×200 mL). The combined organic layers were dried over magnesium sulfate, filtered and concentrated on a rotary evaporator. The residue was column chromatographed using 300 mL silica gel and gradient elution with hexane/ethyl acetate (100–0%). This provided 1.706 g (3.88 mmol, 86%) of the desired quinoline ester. Electrospray Mass Spec 441.1 $(M+H)^+$.

EXAMPLE 26

4-[Methyl-(4-methoxy-benzenesulfonyl)-amino]-6-phenylethynyl-quinoline-3-carboxylic acid ethyl ester Combining the procedures of examples 14 and 25, and substituting phenylacetylene for vinyltin, N-ethyl-4-methoxybenzenesulfonamide for N-benzyl-4-methoxybenzenesulfonamide, the intermediate 4-[ethyl-(4-methoxy-benzene-sulfonyl)-amino]-6-phenylethynyl-quinoline-3-carboxylic acid ethyl ester is obtained from ethyl -4-chloro-3-quinolinecarboxylate. Electrospray Mass Spec 515.3 $(M+H)^+$.

EXAMPLE 27

4-[Ethyl-(4-methoxy-benzenesulfonyl)-amino]-8-vinyl-quinoline-3-carboxylic acid

In the same manner as described in Example 19, 1.593 g (3.62 mmol) of the product from Example 25 provided 1.333 g (89%) of the desired quinoline acid as a white solid. Electrospray Mass Spec 411.1 $(M-H)^-$.

EXAMPLE 28

4-[Methyl-(4-methoxy-benzenesulfonyl)-amino]-6-phenylethynyl-quinoline-3-carboxylic acid In the same manner as described in Example 19, the title compound was synthesized from the product of Example 26. Electrospray Mass Spec 485.3 $(M-H)^-$.

EXAMPLE 29

4-[Benzyl-(4-methoxy-benzenesulfonyl)-amino]-6-nitro-quinoline-3-carboxylic acid In the same manner as described in Examples 14 and 19, 5.613 g (20.0 mmol) ethyl 4-chloro-6-nitro-3-quinolinecarboxylate provided 2.676 g (27% for two steps) of the title compound as a white solid. Electrospray Mass Spec 492.3 $(M-H)^-$.

EXAMPLE 30

4-[Methyl-(4-methoxy-benzenesulfonyl)-amino]-8-bromo-quinoline-3-carboxylic acid Combining the procedures of example 14 and 19, and substituting N-methyl-4-methoxybenzenesulfonamide for N-benzyl-4-methoxybenzenesulfonamide, the intermediate 8-bromo-4-[methyl-(4-methoxy-benzenesulfonyl)-amino]-quinoline-3-carboxylic acid is obtained. Electrospray Mass Spec 449.2 $(M-H)^-$.

EXAMPLE 31

Diethyl{[(1-phenyl-5-pyrazolyl)amino]methylene}malonate

A mixture of 15.9 g. (0.10 mole) of 1-phenyl-5-aminopyrazole and 21.6 g. (0.10 mole) of diethyl ethoxymethylenemalonate was heated at 115–120° in an oil bath for 2 hours. After cooling, the crystalline mass was recrystallized from hot hexane containing 1% of ethanol. Cooling to room temperature and filtering gave 24.8 g. (75%) of off-white crystals, m.p. 96–97° C.

EXAMPLE 32

Ethyl 4-hydroxy-1-phenyl-1H-pyrazolo[3,4-b]pyridine-5-carboxylate

A mixture of 18.1 g. (0.055 mole) of diethyl {[(1-phenyl-5-pyrazolyl)amino]methylene}malonate and 150 ml of diethyl phthalate was heated at 240–250° for 1 hour. The mixture was chilled and diluted with hexane. Chilling and filtering gave crystals which were washed with hexane and with hexane-ethanol (1:1) to give 11 g. (70%) of off white crystals, m.p. 149–150° C. From a similar small scale run 1.75 g. was recrystallized from 110 ml. of ethanol to give 1.58 g. of off white crystals, m.p. 149–150° C.

EXAMPLE 33

Ethyl 4-chloro-1-phenyl-1H-pyrazolo[3,4-b]pyridine-5-carboxylate

A mixture of 5.76 g (20.33 mmol) of ethyl 4-hydroxy-1-phenyl-1H-pyrazolo[3,4-b]pyridine-5-carboxylate and 15.58 g of phosphorus oxychloride was refluxed 1.5 hr, chilled and poured slowly onto crushed ice. The mixture was filtered and the solid washed with ice-water and dried to give 6.0 g of solid, m.p. 89–91° C.

EXAMPLE 34

Ethyl 4-chloro-1,3-dimethyl-1H-pyrazolo[3,4-b]pyridine-5-carboxylate

Following the procedures of Examples 31, 32 and 33, starting from 1,3-dimethyl-5-aminopyrazole, the chloro-ester is prepared. m.p. 89–90° C.

EXAMPLE 35

Ethyl 4-[benzyl-(4-methoxybenzenesulfonyl)amino]-1,3-dimethyl-1H-pyrazolo[3,4-b]pyridine-5-carboxylate To a solution of 1.16 g (4.2 mmol) of benzyl-(4-methoxybenzene-sulfonyl)amine in 6 ml of anhydrous 1-methyl-2-pyrrolidinone was added 0.168 g (4.2 mmol) of sodium hydride (60% in oil) and the mixture stirred at room temperature until gas evolution ceased. The preceding mixture was added to mixture of 1.01 g (4 mmol) of ethyl 4-chloro-1,3-dimethylpyrazolo[3,4-b]pyridine-5-carboxylate in 2 ml of 1-methyl-2-pyrrolidinone.

The mixture was heated in an oil bath at 50° C. overnight and then was heated in an oil bath at 100° C. for 1.5 days. The mixture was poured into 800 ml of water and extracted with ethyl acetate. The extract was washed with water, 2N citric acid, water, brine and dried ($Na_2SO_4$). The solvent was removed and the residue chromatographed on silica gel with hexane-ethyl acetate (2:1) as eluent to give 0.64 g of product as a solid, mp 170–172°. From a larger scale run of 5.07 g (0.02 mmol) of ethyl 4-chloro-1,3-dimethylpyrazolo[3,4-b]pyridine-5-carboxylate and 8.0 g (0.0289 mmol) of benzyl-(4-methoxybenzenesulfonyl)amine (as sodium anion) in 30 ml of 1-methyl-2-pyrrolidinone heated at 90° C. for 3 days there was obtained 3.65 g of product.

EXAMPLE 36

4-[Benzyl-(4-methoxybenzenesulfonyl)amino]-1,3-dimethyl-1H-pyrazolo[3,4-b]pyridine-5-carboxylic acid A mixture of 0.48 g (0.97 mmol) of ethyl 4-[benzyl-(4-methoxybenzene-sulfonyl)amino]-1,3-dimethyl-1H-pyrazolo[3,4-b]pyridine-5-carboxylate and 0.29 ml of 10N NaOH in 4 ml of tetrahydrofuran-methanol (1:1) was heated in an oil bath at 70° C. for 2 hours and the solvent removed under vacuum. The residue was dissolved in 20 ml of $H_2O$ and the solution extracted with 10 ml of diethyl ether. To the aqueous layer was added 2N citric acid (pH 4–5) and the precipitated solid filtered and washed with $H_2O$ to give a white solid which was dried under vacuum overnight to give crystals, mp 165–167° C.

EXAMPLE 37

4-[Benzyl-(4-methoxybenzenesulfonyl)amino]-1,3-dimethyl-1H-pyrazolo[3,4-b]pyridine-5-carboxylic acid, potassium salt A mixture of 3.60 g (7.28 mmol) of ethyl 4-[benzyl-(4-methoxybenzenesulfonyl)amino]-1,3-dimethyl-1H-pyrazolo[3,4-b]pyridine-5-carboxylate and 0.44 g (7.84 mmol) of potassium hydroxide (pellet) in 15 ml of methanol-water (1:1) was refluxed overnight. An additional 40 mg of potassium hydroxide was added and the mixture refluxed for 4 hours (all the solid dissolved). The solvent was removed under vacuum and toluene added and removed under vacuum. The residue was triturated with ethyl acetate, filtered and the solid washed with ethyl acetate to give 3.8 g of product as a white solid.

EXAMPLE 38

Ethyl 4-[(4-methoxybenzenesulfonyl)pyridin -3-ylmethylamino]-1,3-dimethyl-1H-pyrazolo[3,4-b]pyridine-5-carboxylate To a solution of 1.39 g (5 mmol) of (4-methoxybenzenesulfonyl)(3-pyridinylmethyl) amine in 4 ml of anhydrous 1-methyl-2-pyrrolidinone was added 0.2 g (5 mmol) of sodium hydride (60% in oil) and the mixture stirred at room temperature until gas evolution ceased. To this mixture was added 1.15 g (4.54 mmol) of ethyl 4-chloro-1,3-dimethylpyrazolo[3,4-b]pyridine-5-carboxylate and 2 ml of anhydrous 1-methyl-2-pyrrolidinone. The mixture was stirred in a sealed tube under nitrogen in an oil bath at 90° C. for 3 days. The mixture was cooled, poured into water and extracted with ethyl acetate. The extract was washed with $H_2O$, brine and dried ($Na_2SO_4$). The solution was filtered through a thin pad of hydrous magnesium silicate and the filter pad washed with ethyl acetate. The filtrate was concentrated to dryness under vacuum to give 1.3 g of solid. Chromatography on silica gel with ethyl acetate as solvent gave 0.35 g of product as a solid, mp 152–154° C.

EXAMPLE 39

4-[(4-Methoxybenzenesulfonyl)pyridin-3-ylmethylamino]-1,3-dimethyl-1H-pyrazolo[3,4-b]pyridine-5-carboxylic acid A mixture of 1.34 g (2.7 mmol) of ethyl 4-[(4-methoxybenzenesulfonyl)pyridin-3-ylmethylamino]-1,3-dimethyl-1H-pyrazolo[3,4-b]pyridin-5-carboxylate, 2.97 ml of 1N potassium hydroxide in 7.8 ml of ethanol and 4.83 ml of water was refluxed for 20 hr. Another 0.54 ml of 1N potassium hydroxide was added and the mixture refluxed 4 hrs. The solvent was removed under vacuum and toluene added and removed under vacuum. The residue was dissolved in water (20 ml) and extracted with ethyl acetate. The aqueous layer was acidified with 2 N citric acid and the precipitated solid filtered off and washed with water. The solid was dried under vacuum to give 0.98 g of solid, mp 256–258° C.

EXAMPLE 40

4-[(4-Methoxybenzenesulfonyl)pyridin-3-ylmethylamino]-1,3-dimethyl-1H-pyrazolo[3,4-b]pyridine-5-carboxylic acid, potassium salt A mixture of 0.34 g (0.68 mmol) of ethyl 4-[(4-methoxybenzenesulfonyl)pyridin-3-ylmethylamino]-1,3-dimethyl-1H-pyrazolo[3,4-b]pyridine-5-carboxylate and 0.748 ml of 1 N potassium hydroxide in 4 ml of ethanol-water (1:1) was refluxed for 24 hr. The solvent was removed under vacuum and to the residue was added toluene. The solvent was removed under vacuum to remove the water and the residue triturated with ethyl acetate to give the product as a solid, mp 160–167° C.

EXAMPLE 41

4-[Benzyl-(4-methoxybenzenesulfonyl)amino]-1-phenyl-1H-pyrazolo[3,4-b]pyridine-5-carboxylic acid Following the procedure of Example 35, the product of Example 33 is reacted with benzyl-(4-methoxybenzenesulfonyl)amine and sodium hydride to provide ethyl 4-[benzyl-(4-methoxybenzenesulfonyl)amino]-1-phenyl-1H-pyrazolo[3,4-b]pyridine-5-carboxylate. m.p. 124°–126° C.

Following the procedure of Example 36, the above ester is hydrolyzed to provide 4-[benzyl-(4-methoxybenzenesulfonyl)amino]-1-phenyl-1H-pyrazolo-[3,4-b]pyridine-5-carboxylic acid. m.p. 108°–110° C.

EXAMPLE 42

4-[(4-Methoxybenzenesulfonyl)pyridin-3-ylmethylamino]-1-phenyl-1H-pyrazolo[3,4-b]pyridine-5-carboxylic acid Following the procedure of Example 38, the product of Example 33 is reacted with (4-methoxybenzenesulfonyl)(3-pyridinylmethyl) amine and sodium hydride to provide ethyl 4-[(4-methoxybenzenesulfonyl)pyridin-3-ylmethylamino]-1-phenyl-1H-pyrazolo[3,4-b]pyridine-5-carboxylate. m.p. 89°–91° C.

Following the procedure of Example 39, the above ester is hydrolyzed to provide 4-[(4-methoxybenzenesulfonyl)pyridin-3-ylmethylamino]-1-phenyl-1H-pyrazolo-[3,4b]pyridine-5-carboxylic acid. m.p. 136°–138° C.

EXAMPLE 43

Ethyl 4-chloro-1-phenyl-3-methyl-1H-pyrazolo[3,4-b]pyridine-5-carboxylate

Following the procedure of Example 31, starting with 1-phenyl-3-methyl-5-aminopyrazole, diethyl{[(1-phenyl-3-methyl-5-pyrazolyl)amino]methylene}malonate is obtained. m.p. 70°–72° C.

Following the procedure of Example 32, the methylene malonate is converted into ethyl 4-hydroxy-1-phenyl-3-methyl-1H-pyrazolo[3,4-b]pyridine-5-carboxylate. m.p. 132°–134° C.

Following the procedure of Example 33 the preceding compound is converted to the product of the Example, m.p. 108–110° C.

EXAMPLE 44

4-[Benzyl-(4-methoxybenzenesulfonyl)amino]-1-phenyl-3-methyl-1H-pyrazolo[3,4b]pyridine-5-carboxylic acid Following the procedure of Example 35, the product of Example 43 is reacted with benzyl-(4-methoxybenzenesulfonyl)amine and sodium hydride to provide ethyl 4-[benzyl-(4-methoxybenzenesulfonyl)amino]-1-phenyl-3-methyl-1H-pyrazolo[3,4-b]pyridine-5-carboxylate. m.p. 164°–166° C.

Following the procedure of Example 36, the above ester is hydrolyzed to provide 4-[benzyl-(4-methoxybenzenesulfonyl)amino]-1-phenyl-3-methyl-1H-pyrazolo[3,4-b]pyridine-5-carboxylic acid. m.p. 246°–248° C.

EXAMPLE 45

4-[(4-Methoxybenzenesulfonyl)pyridin-3-ylmethylamino]-1phenyl-3-methyl-1H-pyrazolo[3,4-b]pyridine-5-carboxylic acid Following the procedure of Example 38, the product of Example 43 is reacted with (4-methoxybenzenesulfonyl)(3-pyridinylmethyl) amine and sodium hydride to provide ethyl-4-[(4-methoxybenzenesulfonyl)pyridin-3-ylmethylamino]-1-phenyl-3-methyl-1H-pyrazolo[3,4-b]pyridine-5-carboxylate. m.p. 148°–150° C.

Following the procedure of Example 39, the above ester is hydrolyzed to provide 4-[(4-methoxybenzenesulfonyl)pyridin-3-ylmethylamino]-1-phenyl-3-methyl-1H-pyrazolo[3,4-b]pyridine-5-carboxylic acid. m.p. 235°–236° C.

EXAMPLE 46

4-[(4-Methoxybenzenesulfonyl)pyridin-3-ylmethylamino]-3-methylisothiazolo[5,4-b]pyridine-5-carboxylic Acid To a stirred mixture of 0.366 g (8.4 mmol) of sodium hydride (60% in oil) in 10 ml of dry 1-methyl-2-pyrrolidinone was added (portionwise) 2.34 g (8.4 mmol) of methyl (4-methoxybenzenesulfonyl)pyridin-3-ylmethyl-amine. The mixture was stirred at room temperature until gas evolution ceased and 1.80 g of (7.0 mmol) of ethyl 4-chloro-3-methylisothiazolo[5,4-b]pyridine-5-carboxylate added. The mixture was heated at 80–90° C. for 44 hours, the solvent removed under vacuum and the residue diluted with water. The mixture was extracted with ethyl acetate and the extract washed with 2N citric acid, $H_2O$, 1 N $NaHCO_3$, brine and dried ($Na_2SO_4$). The solution was filtered through a thin pad of hydrous magnesium silicate and the pad washed with ethyl acetate. The filtrate was concentrated to dryness to give 2.39 g of ethyl 4-[(4-methoxybenzenesulfonyl)-pyridin-3-ylmethylamino]-3-methylisothiazolo[5,4-b]pyridine-5-carboxylate as a yellow solid, m.p. 142–144° C.

Anal. for $C_{23}H_{22}N_4O_5S_2$; Calc: C, 55.4; H, 4.5; N, 11.2. Found: C, 55.5; H, 4.3; N, 11.1.

Following the procedure of Example 39, a 2.25 g sample of the above ester was hydrolysed with KOH to give 0.46 g of 4-[(4-methoxybenzenesulfonyl)pyridin-3-ylmethylamino]-3-methylisothiazolo[5,4-b]pyridine-5-carboxylic acid as a white solid, m.p. 234–236° C.

Anal. for $C_{21}H_{18}N_4O_5S_2$; Calc: C, 53.6; H, 3.9; N, 11.9. Found: C, 53.5; H, 3.8; N, 11.8.

EXAMPLE 47

4-[(4-Methoxybenzenesulfonyl)pyridin-3-ylmethylamino]-3-methylisoxazolo[5,4-b]pyridine-5-carboxylic Acid Following the procedure of Example 46, 1.7 g (7 mmol) of ethyl 4-chloro-3-methylisoxazolo[5,4-b]pyridine-5-carboxylate was reacted with 2.92 g (0.0105 mmol) of (4-methoxybenzenesulfonyl)pyridin-3-ylmethyl-amine to give 1.01 g of ethyl 4-[(4-methoxy-benzenesulfonyl)pyridin-3-yl-methylamino]-3-methylisoxazolo[5,4-b]pyridine-5-carboxylate as a white solid, m.p. 128–130° C.

Anal. for $C_{23}H_{22}N_4O_6S$; Calc: C, 57.3; H, 4.6; N, 11.6. Found: C, 57.3; H, 4.7; N, 11.5.

A mixture of 1.01 g (2.1 mmol) of the preceding compound in 10 ml of tetrahydrofuran and 2.93 ml of 1 N NaOH was stirred at room temperature overnight and the solvent removed. The residue was diluted with $H_2O$ and acidified with 2N citric acid (pH 4). The solid was filtered off and washed with $H_2O$ to give 0.88 g of 4-[(4-methoxybenzenesulfonyl)pyridin-3-ylmethylamino]-3-methylisoxazolo[5,4-b]pyridine-5-carboxylic acid as a white solid, m.p. 244–246° C.

Anal. for $C_{21}H_{18}N_4O_6S$; Calc: C, 55.5; H, 4.0; N, 12.3. Found: C, 55.2; H, 4.0; N, 12.2.

EXAMPLE 48

7-[(4-Methoxybenzenesulfonyl)pyridin-3-ylmethylamino]-2-methylpyrazolo[1,5-a]pyrimidine-6-carboxylic Acid Following the procedure of Example 46, 1.8 (7.5 mmol) of ethyl 7-chloro-2-methyl pyrazolo[1,5-a]pyrimidine-6-carboxylate was reacted with 2.92 g (10.5 mmol) of (4-methoxybenzenesulfonyl)pyridin-3-ylmethyl-amine to give 1.64 g of ethyl 7-[(4-methoxybenzenesulfonyl)pyridin-3-ylmethylamino]-2-methylpyrazolo[1,5-a]pyrimidine-6-carboxylic acid as a yellow solid, m.p. 108–110° C.

Anal. for $C_{23}H_{23}N_5O_5S$; Calc: C, 57.4; H, 4.8; N, 14.5. Found: C, 54.5; H, 4.7; N, 14.4.

A mixture of 1.54 g (3.20 mmol) of the preceding compound, tetrahydrofuran (15 ml) and 4.15 ml of 1 N NaOH was stirred at room temperature overnight and the solvent removed under vacuum. The residue was diluted with $H_2O$ and extracted with diethyl ether and ethyl acetate. The aqueous layer was acidified with 2 N citric acid (pH 5) and the solid filtered off and washed with $H_2O$. The solid was dried at 76° C. in a vacuum oven to give 1.03 g of 7-[(4-methoxybenzenesulfonyl)pyridin-3-ylmethylamino]-2-methylpyrazolo[1,5-a]pyrimidine-6-carboxylic acid as an off-white solid, m.p. 249–251° C.

Anal. for $C_{21}H_{19}N_5O_5S$; Calc: C, 55.6; H, 4.2; N, 15.4. Found: C, 55.2; H, 4.2; N, 15.6.

EXAMPLE 49

Ethyl 4-Chloro-1,6-dimethyl-1H-pyrazolo[3,4,b]pyridine-5-carboxylate

To a solution of 10.0 g (59.1 mmol) of ethyl 5-amino-1-methylpyrazole-4-carboxylate in 150 ml of p-xylenes was added to a solution of 10.25 g (65.01 mmol) of ethyl trans-3-ethoxycrotonate in 30 ml of p-xylenes. The mixture was refluxed for overnight. The solution was chilled in an ice bath and 24.3 ml of sodium ethoxide (21% by wt in ethanol) was added dropwise. The mixture was refluxed for 3.5 hrs. The mixture was concentrated under vacuum and 350 ml of ethyl acetate added to the residue. The solution was washed with 150 ml of each of 2N citric acid, $H_2O$, brine and dried ($Na_2SO_4$). The solution was filtered through a pad of hydrous magnesium silicate and the solvent removed to give an off-white solid. Trituration with ethyl acetate followed by chilling the mixture and filtration gave 7.8 g of ethyl 4-hydroxy-1,6-dimethyl-1H-pyrazolo[3,4-b]pryridine-5-carboxylate as white crystals, mp 103–105° C.

The preceding compound (3.0 g) in 8 ml of $POCl_3$ was refluxed for 2.5 hrs. The mixture was chilled and poured slowly onto crushed ice. The solid was filtered off, washed with water and dried at 50° C. under vacuum to give 2.3 g of off-white crystals, mp 64–66° C.

EXAMPLE 50

Ethyl 7-Chloro-2,3-dimethylimidazo[4,5-b]pyridine-6-carboxylate

Following the general procedure described in J. Chem. Soc. Perkin Trans. 1, 2789 (1992) a mixture of 1,2-dimethyl-5-nitroimidazole (8.46 g; 0.06 M), diethyl ethoxymethylenemalonate (13.08 g; 0.06 M) and 2.11 g of 5% Pd on carbon in 135 ml of dioxane was reduced in a Parr Hydrogenator at 35 to 40 psi of hydrogen for 29 hours. The mixture was filtered through diatomaceous earth and the solvent removed to give a brown oil. This oil was dissolved in 100 ml of 2 N HCl and the pH adjusted to pH 5 with 10 N NaOH. The mixture was extracted twice with 100 ml of ethyl acetate (extract discarded). The pH was adjusted to pH 7 and extracted with 150 ml of ethyl acetate and then the pH was adjusted to pH 9 and again extracted twice with 150 ml of ethyl acetate. The pH 7 and pH 9 extracts were combined and washed with brine and dried over $Na_2SO_4$. The solution was filtered through a thin pad of hydrous magnesium silicate and the filtrate concentrated to dryness to give 7.61 g of 5-[2,2-bis(ethoxycarbonyl)-1-vinylamino]-1,2-dimethylimidazole (diethyl[(1,2-dimethyl-imidazol-5-yl)aminomethylene]malonate) as a brown oil.

A mixture of the preceding compound (7.9 g) and 35 ml of $POCl_3$ was refluxed for 7 hours under nitrogen and then concentrated under vacuum. The black residue was poured onto crushed ice (with stirring) and the mixture brought to pH 5 with 5 N NaOH. The mixture was extracted with 150 ml of ethyl acetate, 200 ml of diethyl ether and 200 ml of $CH_2Cl_2$. Each extract was washed with 1N $NaHCO_3$, brine and dried ($Na_2SO_4$). The solutions were combined and filtered through a thin pad of hydrous magnesium silicate. The filtrate was concentrated to dryness under vacuum to give 4.1 g of ethyl 7-chloro-2,3-dimethylimidazo[4,5-b]pyridine-6-carboxylate as a tan solid, m.p. 85–90° C. A sample crystallized from diethyl ether gave crystals, m.p. 117–119° C., Anal. for $C_{11}H_{12}ClN_3O_2 \cdot 1/2H_2O$ Calc. C, 48.8; H, 4.6; N, 15.9; Found C, 50.3; H, 5.6; N, 16.0.

EXAMPLE 51

Methyl 4-Chloro-2-methylthieno[3,4-b]pyridine-3-carboxylate

A mixture of 10.0 g (63.6 mmol) of methyl 3-aminothiophene-4-carboxylate, 10.1 g (63.6 mmol) of ethyl (trans)-3-ethoxycrotonate and 40 mg of p-toluenesulfonic acid, monohydrate in 50 ml of p-xylenes was refluxed overnight and the solvent removed under vacuum. To the residue was added 20 ml of p-xylenes, and 23.7 ml of sodium ethoxide (21% by wt) (63.6 mmol) in ethanol and the mixture refluxed for 3 h. The solvent was removed, the residue diluted with $H_2O$ and the pH adjusted to pH 4 with 1 N HCl. The precipitate was filtered, washed with water and ethyl acetate to give 4.95 g of 4-hydroxy-2-methyl-thieno[3,4-b]pyridine-3-carboxylic acid as a brown solid.

The preceding compound (1.4 g) was dissolved in 10 ml of dry methanol and HCl gas bubbled into the solution for 10 min. The solution was stirred overnight at room temperature and the solvent removed under vacuum. The residue was dissolved in ethyl acetate and the solution washed with saturated $NaHCO_3$, brine and dried ($Na_2SO_4$). The solvent was removed to give a solid which was triturated with ethyl acetate. The mixture was cooled and filtered to give 0.765 g of methyl 4-chloro-2-methylthieno[3,4-b]pyridine-3-carboxylate as a yellow solid.

EXAMPLE 52

Methyl and Ethyl 7-Chloro-5-methyl-thieno[3,2-b]pyridine-6-carboxylate

Following the procedure described in J. Med. Chem. 33, 2640 (1990), a mixture of 10 g (63.6 mmol) of methyl 3-aminothiophene-2-carboxylate (10.1 g) (63.6 mmol) of ethyl (trans)-3-ethoxycrotonate and 40 mg of p-toluenesulfonic acid monohydrate in 80 ml of xylene was refluxed overnight. The solvent was removed under vacuum and the residue dissolved in ethyl acetate. The solution was washed with $H_2O$, 2 N citric acid, 1 N $NaHCO_3$, brine and dried ($Na_2SO_4$). The solid 16 g was chromatographed on silica gel with hexane-ethyl acetate (5:1) to give 6.65 g of ethyl 3-[(2-methyoxycarbonyl-3-thienyl)amino]crotonate as a yellow oil. To a sample of 0.269 g (1 mmol) of the preceding compound in 3.5 ml of xylenes (chilled in an ice bath) was added 44 mg (1.1 mmol) of NaH (60% in oil), The mixture was refluxed for 3 hours and the solvent removed. The residue diluted with water and extracted with ethyl acetate. The aqueous layer was acidified (1 N HCl) to pH 4 and the mixture extracted with ethyl acetate. The extract was washed with brine, dried over $Na_2SO_4$ and the solvent removed to give 190 mg of a mixture (1:1) of methyl 7-hydroxy-5-methylthieno[3,2-b]pyridine-6-carboxylate and ethyl 7-hydroxy-5-methylthieno[3,2-b]pyridine-6-carboxylate as a solid. The preceding ethyl ester was prepared in the following manner.

A mixture of 5.0 g (31.8 mmol) of methyl 3-aminothiophene-2-carboxylate, 5.03 g (31.8 mmol) of ethyl (trans)-3-ethoxycrotonate and 20 mg of p-toluenesulfonic acid monohydrate in 50 ml of p-xylenes was refluxed 1 hour and allowed to stand 2 days at room temperature. The mixture was concentrated under vacuum and then cooled (ice bath). To the solution was added 12.4 ml of a solution of sodium ethoxide (21% by wt) in ethanol. The mixture was refluxed for 2 hours and the solvent removed. The residue was partitioned between $H_2O$ and diethyl ether and the $H_2O$ layer separated and acidified to pH 4 with 1 N HCl. The mixture was extracted with ethyl acetate and the extract washed with brine and dried ($Na_2SO_4$). The solvent was removed to give 2.2 g of brown solid. The solid was triturated with ethyl acetate, chilled and filtered to give 1.0 g of ethyl 7-hydroxy-5-methylthieno[3, 2-b]pyridine-6-carboxylate as a light tan solid (mass spectrum (ES) 238 (M+H).

A mixture of the preceding compound (0.985 g) and 4 ml of $POCl_3$ was refluxed 2 hours and the mixture poured onto crushed ice. The mixture was extracted with ethyl acetate and the extract concentrated to dryness. The residue was dissolved in $CH_2Cl_2$ and the solution washed with $H_2O$ and dried over $Na_2SO_4$. The solution was filtered through a thin pad of hydrous magnesium silicate and the filtrate concentrated to dryness to give 0.62 g of ethyl 7-chloro-5-methylthieno[3,2-b]pyridine-6-carboxylate as a yellow oil; thin layer chromatography on silica gel; Rf=0.9; ethyl acetate-hexane (1:1).

EXAMPLE 53

Ethyl 1,3-dimethyl-4-methylamino-1H-pyrazolo[3, 4-b]pyridine-5-carboxylate

A mixture of 1.268 g (5 mmol) of ethyl 4-chloro-1,3-dimethyl-1H-pyrazolo[3,4-b]pyridine-5-carboxylate and 7.5 ml (15 mmol) of methylamine in tetrahydrofuran (2.0 molar solution) was stirred at room temperature overnight and refluxed for 2 hours. The solvent was removed to give a white solid. The solid was dissolved in ethyl acetate and the solution washed with $H_2O$, 1M $NaHCO_3$, brine and dried ($Na_2SO_4$). The solvent was removed to give a white solid. Crystallization from ethyl acetate gave 0.715 g of white solid; Mass spectrum (ES) 249.2 (M+H).

Following the above procedure, reaction of methylamine with the appropriate chloroheterocyclicpyridine gives the following derivatives.

EXAMPLE 54

Ethyl 1,6-dimethyl-4-methylamino-1H-pyrazolo[3, 4-b]pyridine-5-carboxylate

EXAMPLE 55

Ethyl 1-Methyl-4-methylamino-1H-pyrazolo[3,4-b] pyridine-5-carboxylate

EXAMPLE 56

Ethyl 1-Ethyl-4-methylamino-1H-pyrazolo[3,4-b] pyridine-5-carboxylate

EXAMPLE 57

Ethyl 1-Phenylmethyl-4-methylamino-1H-pyrazolo [3,4-b]pyridine-5-carboxylate

EXAMPLE 58

Ethyl 1-Phenyl-4-methylamino-1H-pyrazolo[3,4-b] pyridine-5-carboxylate

EXAMPLE 59

Ethyl 1-Methyl-3-phenyl-4-methylamino-1H-pyrazolo[3,4-b]pyridine-5-carboxylate

EXAMPLE 60

Ethyl 3-Methyl-1-phenyl-4-methylamino-1H-pyrazolo[3,4-b]pyridine-5-carboxylate

EXAMPLE 61

Ethyl 3-Methyl-4-methylaminoisothiazolo[5,4-b] pyridine-5-carboxylate

EXAMPLE 62

Ethyl 3-Methyl-4-methylaminoisoxazolo[5,4-b] pyridine-5-carboxylate

EXAMPLE 63

Ethyl 2,3-Dimethyl-7-methylaminoimidazo[4,5-b] pyridine-6-carboxylate

EXAMPLE 64

Ethyl 4-Methylaminothieno[2,3-b]pyridine-5-carboxylate

EXAMPLE 65

Ethyl 4-Methylaminothieno[3,2-b]pyridine-5-carboxylate

EXAMPLE 66

Ethyl 4-Methylaminothieno[3,4-b]pyridine-5-carboxylate

EXAMPLE 67

N-Methyl-4-fluorobenzenesulfonamide

A mixture of 125 ml of methylamine (0.25 molar) in tetrahydrofuran and 13.9 ml (0.10 mol) of triethylamine was chilled in an ice bath. To this chilled solution was added dropwise 19.4 g (0.10 mol) of 4-fluorobenzenesulfonyl chloride in 150 ml of $CH_2Cl_2$ was added and the mixture refluxed for 2 hours and then stirred overnight at room temperature. The mixture was with $CH_2Cl_2$, washed with $H_2O$, 2N citric acid, brine and dried ($Na_2SO_4$). The solution was filtered through a pad of hydrous magnesium silicate and the filtrate concentrated to dryness under vacuum to give 18.0 g of white solid, mp 67–70° C.

As described in the procedure of the above Example, the following 4-fluorobenzenesulfonyl analogues may be prepared.

EXAMPLE 68

N-Ethyl-4-fluorobenzenesulfonamide

EXAMPLE 69

N-Butyl-4-fluorobenzenesulfonamide

EXAMPLE 70

N-Benzyl-4-fluorobenzenesulfonamide

EXAMPLE 71

N-(3-Pyridinylmethyl)-4-fluorobenzenesulfonamide

EXAMPLE 72

Ethyl 4-[(4-Fluorobenzenesulfonyl)methylamino]-1,3-dimethyl-1H-pyrazolo[3,4-b]pyridine-5-carboxylate A mixture of 2.53 g (0.01 mol) of ethyl 4-chloro-1,3-dimethyl-1H pyrazolo[3,4-b]pyridine-5-carboxylate, 1.89 g (0.01 mol) of N-methyl-4-fluorobenzenesulfonamide, 6.91 g (0.05 mol) of anhydrous $K_2CO_3$, 0.143 g of 18-crown-6 and 70 ml of anhydrous 1-methyl-2-pyrrolidinone was stirred and heated at 100° C. for 17 hours. The solvent was removed under vacuum and water added to the residue. The mixture was extracted with $CH_2Cl_2$, and the extract washed with $H_2O$, brine and dried ($Na_2SO_4$). The solution was filtered through a pad of hydrous magnesium silicate and the filtrate concentrated to dryness under vacuum to give 4.98 g of an oil. This oil was chromatographed on a silica gel column with ethyl acetate-hexane(2:3) as solvent to give 3.15 g of solid, mp 107–109° C.

Following the above procedure the following derivatives may be prepared.

EXAMPLE 73

Ethyl 4-[Benzyl-(4-fluorobenzenesulfonyl)amino]-1,3-dimethyl-1H-pyrazolo[3,4-b]pyridine-5-carboxylate

EXAMPLE 74

Ethyl 4-[Benzyl-(4-fluorobenzenesulfonyl)amino]-1-phenyl-3-methyl-1H-pyrazolo[3,4-b]pyridine-5-carboxylane

EXAMPLE 75

Ethyl 4-[Benzyl-(4-fluorobenzenesulfonyl)amino]-1-phenyl-1H-pyrazolo[3.4-b]pyridine-5-carboxylate

EXAMPLE 76

Ethyl 4-[Benzyl-(4-fluorobenzenesulfonyl)amino]-1-methyl-3-phenyl-1H-pyrazolo[3,4-b]pyridine-5-carboxylate

EXAMPLE 77

Ethyl 4-[(4-Flurobenzenesulfonyl)methylamino]-1-phenyl-1H-pyrazolo[3,4-b]pyridine-5-carboxylate

EXAMPLE 78

Ethyl 4-[(4-Fluorobenzenesulfonyl)methylamino]-1-phenyl-3-methyl-1H-pyrazolo[3,4-b]pyridine-5-carboxylate

EXAMPLE 79

Ethyl 4-[(4-Fluorobenzenesulfonyl)methylamino]-1-methyl-3-phenyl-1H-pyrazolo[3,4-b]pyridine-5-carboxylate

EXAMPLE 80

Ethyl 4-[(4-Fluorobenzenesulfonyl)methylamino]-1-phenylmethyl-3-methyl-1H-pyrazolo[3,4-b]pyridine-5-carboxylate

EXAMPLE 81

Ethyl 4-[(4-Fluorobenzenesulfonyl)methylamino]-1-ethyl-3-phenyl-1H-pyrazolo[3,4-b]pyridine-5-carboxylate

EXAMPLE 82

Ethyl 4-[(4-Fluorobenzenesulfonyl)methylamino]-3-methylisothiazolo[4,5-b]pyridine-5-carboxylate

EXAMPLE 83

Ethyl 7-[(4-Fluorobenzenesulfonyl)methylamino]-2,3-dimethylimidazo[4,5-b]pyridine-6-carboxylate

EXAMPLE 84

Methyl 4-[(4-Fluorobenzenesulfonyl)methylamino]-2-methylthieno[3,4-b]pyridine-3-carboxylate

EXAMPLE 85

Methyl 7-[(4-Fluorobenzenesulfonyl)methylamino]-5-methylthieno[3,2-b]pyridine-6-carboxylate

EXAMPLE 86

Ethyl 4-[(4-Fluorobenzenesulfonyl)methylamino]thieno[3,4-b]pyridine-3-carboxylate

EXAMPLE 87

Ethyl 7-[(4-Fluorobenzenesulfonyl)methylamino]thieno[3,2-b]pyridine-6-carboxylate

EXAMPLE 88

Ethyl 4-[(4-Fluorobenzenesulfonyl)methylamino]thieno[2,3-b]pyridine-5-carboxylate

EXAMPLE 89

Ethyl 4-[(4-Fluorobenzenesulfonyl)methylamino]-5-chlorothieno[3,4-b]pyridine-3-carboxylate

EXAMPLE 90

Ethyl 4-[(4-Fluorobenzenesulfonyl)methylamino]-7-chlorothieno[3,4-b]pyridine-3-carboxylate

EXAMPLE 91

Ethyl 7-[(4-Fluorobenzenesulfonyl)methylamino]-3-chlorothieno[3,2-b]pyridine-6-carboxylate

EXAMPLE 92

Ethyl 4-[(4-Fluorobenzenesulfonyl)methylamino]-3-chlorothieno[2,3-b]pyridine-5-carboxylate

EXAMPLE 93

Ethyl 4-[(4-Fluorobenzenesulfonyl)methylamino]-2-chlorothieno[2,3-b]pyridine-5-carboxylate

EXAMPLE 94

Ethyl 4-[(4-Fluorobenzenesulfonyl)methylamino]-7-methylthieno[3,4-b]pyridine-3-carboxylate

EXAMPLE 95

4-[(4-Fluorobenzenesulfonyl)methylamino]-1,3-dimethyl-1H-pyrazolo[3,4-b]pyridine-5-carboxylic acid To a solution of 0.284 g (0.7 mmol) of ethyl 4-[(4-fluorobenzene-sulfonyl)methylamino]3-dimethyl-1H-pyrazolo[3,4-b]pyridine-5-carboxylate in 5 ml of tetrahydrofuran was added 0.490 ml (2.45 mmol) of 5N NaOH. The mixture was stirred at room temperature overnight and 2 ml of ethanol added. The solution was refluxed for 2.5 hours ,the solvent removed under vacuum and 2N citric acid added to the residue (pH 4–5). The white solid which separated was filtered off, washed with the $H_2O$ and dried under vacuum to give 0.24 g of crystals, mp 275–276° C.

Anal. For $C_{16}H_{15}FN_4O_4S$; Calc: C, 50.8; H, 4.0; N, 14.8 Found: C, 51.6; H, 4.2; N, 14.7.

EXAMPLE 96

4-[(4-But-2-ynyloxybenzenesulfonyl)methylamino]-1,3-dimethyl-1H-pyrazolo[3,4-b]pyridine-5-carboxylic acid (A) To 3.5 mmol of NaH in 3 ml of dry N,N-dimethylformamide cooled in an ice bath is added dropwise 3.5 mmol of 2-butyn-1-ol. To this mixture is added mmol of 4-[(4-fluorobenzenesulfonyl)methylamino]-1,3 dimethyl-1H-pyrazolo[3,4-b]pyridine-5-carboxylic acid and the mixture is stirred for 2 hours. The mixture is poured into $H_2O$, and extracted with ethyl acetate. The aqueous layer is acidified with ethyl acetate extracted with ethyl acetate, and the extract concentrated to give a solid.

(B) To a mixture of 0.14 g (3.5 mmol) of NaH cooled in an ice bath was added dropwise, 0.267 ml (3.5 mmol) of 2-butyn-1-ol. After 10 minutes, 0.406 g (1 mmol ) of ethyl 4-[4-fluorobenzenesulfonyl)methylamino]-1,3-dimethyl-1H-pyrazolo[3,4]pyridine-5-carboxylate was added and the mixture was stirred at room temperature for 3 hours. The mixture was poured into water and extracted with ethyl acetate. The aqueous layer was acidified with 2N citric acid and extracted with ethyl acetate. This extract was washed with water, brine, dried ($Na_2SO_4$) and the solvent removed to give a 0.17 of impure solid. The mass spectrum (electrospray) showed a product peak at 427 (M–H).

EXAMPLE 97

Ethyl 8-bromo-4-[{[4-(2-butynyloxy)phenyl]sulfonyl}(methyl)amino]-3-quinolinecarboxylate To a room temperature solution of 1.97 g (6.27 mmol) of the product of Example 5 in 40 mL of dimethylformamide was added 0.276 g of 60% sodium hydride (6.9 mmol). After 1 hour 1.5 g (6.27 mmol) of ethyl 8-bromo-4-chloro-3-quinolinecarboxylate was added and the mixture heated to 80° C. After 18 hours the reaction mixture was cooled to room temperature and ethyl acetate and water were added. The organic phase was washed with water (5×) and dried over anhydrous magnesium sulfate. Filtration and concentration in vacuo gave an oil (3.44 g) which was chromatographed on silica gel (hexane/ethyl acetate) to give ethyl 8-bromo-4-[{[4-(2-butynyloxy)phenyl]sulfonyl}(methyl)amino]-3-quinolinecarboxylate as a foam (2.79 g). Electrospray Mass Spec 517 and 519 $(M+H)^+$

EXAMPLE 98

8-Bromo-4-[{[4-(2-butynyloxy)phenyl]sulfonyl}(methyl)amino]-3-quinolinecarboxylic acid Ethyl 8-bromo-4-[{[4-(2-butynyloxy)phenyl]sulfonyl}(methyl)amino]-3-quinolinecarboxylate (0.52 g, 1.0 mmol), the product of Example 97, was treated with 1 N aqueous sodium hydroxide (1.1 mL) in 1:1 methanol:water (6 mL) to give 0.390 g of 8-bromo-4-[{[4-(2-butynyloxy)phenyl]sulfonyl}(methyl)amino]-3-quinolinecarboxylic acid as an off-white powder. Electrospray Mass Spec 489 and 490.9 $(M+H)^+$

EXAMPLE 99

8-Bromo-4-[{[4-(2-butynyloxy)phenyl]sulfonyl}(methyl)amino]-N-hydroxy-3-quinolinecarboxamide To oxalyl chloride (0.613 mL of a 2 M solution in dichloromethane) in dichloromethane (1 mL) at 0° C. was added dimethylformamide (0.095 mL). After 15 min a solution of 8-bromo-4-[{[4-(2-butynyloxy)phenyl]sulfonyl}(methyl)amino]-3-quinolinecarboxylic acid (0.30 g, 0.613 mmol), the product of Example 98, in dimethylformamide was added and the resulting reaction mixture was stirred at room temperature for 1 h.

In a separate flask, 1.28 mL of triethylamine was added to a 0° C. mixture of 0.43 g of hydroxylamine hydrochloride in 13 mL of tetrahydrofuran and 3.2 mL of water. After this mixture stirred for 15 min at 0° C., the acid chloride solution was added to it in one portion and the resulting solution was allowed to warm to room temperature and stirred for another 18 h. Ethyl acetate and aqueous sodium bicarbonate were then added to the reaction flask. The organic phase was washed with aqueous sodium bicarbonate (3×) and dried over anhydrous potassium carbonate. Concentration in vacuo and trituration with diethyl ether gave 8-bromo-4-[{[4-(2-butynyloxy)phenyl]sulfonyl}(methyl)amino]-N-hydroxy-3-quinolinecarboxamide as a yellow powder (200 mg). Electrospray Mass Spec 503.9 and 506 $(M+H)^+$

Pharmacology

Representative compounds of this invention were evaluated as inhibitors of the enzymes MMP-1, MMP-9, MMP-13 and TNF-α converting enzyme (TACE). The standard pharmacological test procedures used, and results obtained which establish this biological profile are shown below.

Test Procedures for Measuring MMP-1 MMP-9, and MMP-13 Inhibition

These standard pharmacological test procedures are based on the cleavage of a thiopeptide substrates such as Ac-Pro-Leu-Gly(2-mercapto-4-methyl-pentanoyl)-Leu-Gly-OEt by the matrix metalloproteinases MMP-1, MMP-13 (collagenases) or MMP-9 (gelatinase), which results in the release of a substrate product that reacts colorimetrically with DTNB (5,5'-dithiobis(2-nitro-benzoic acid)). The enzyme activity is measured by the rate of the color increase. The thiopeptide substrate is made up fresh as a 20 mM stock in 100% DMSO and the DTNB is dissolved in 100% DMSO as a 100 mM stock and stored in the dark at room temperature. Both the substrate and DTNB are diluted together to 1 mM with substrate buffer (50 mM HEPES pH 7.5, 5 mM $CaCl_2$) before use. The stock of enzyme is diluted with buffer (50 mM HEPES, pH 7.5, 5 mM $CaCl_2$, 0.02% Brij) to the desired final concentration. The buffer, enzyme, vehicle or inhibitor, and DTNB/substrate are added in this order to a 96 well plate (total reaction volume of 200 µl) and the increase in color is monitored spectrophotometrically for 5 minutes at 405 nm on a plate reader and the increase in color over time is plotted as a linear line.

Alternatively, a fluorescent peptide substrate is used. In this test procedure, the peptide substrate contains a fluorescent group and a quenching group. Upon cleavage of the substrate by an MMP, the fluorescence that is generated is quantitated on the fluorescence plate reader. The assay is run in HCBC assay buffer (50 mM HEPES, pH 7.0, 5 mM $Ca^{+2}$, 0.02% Brij, 0.5% Cysteine), with human recombinant MMP-1, MMP-9, or MMP-13. The substrate is dissolved in methanol and stored frozen in 1 mM aliquots. For the assay, substrate and enzymes are diluted in HCBC buffer to the desired concentrations. Compounds are added to the 96 well plate containing enzyme and the reaction is started by the addition of substrate. The reaction is read (excitation 340 nm, emission 444 nm) for 10 min. and the increase in fluorescence over time is plotted as a linear line.

For either the thiopeptide or fluorescent peptide test procedures, the slope of the line is calculated and represents the reaction rate. The linearity of the reaction rate is confirmed ($r^2>0.85$). The mean (x±sem) of the control rate is calculated and compared for statistical significance (p<0.05) with drug-treated rates using Dunnett's multiple comparison test. Dose-response relationships can be generated using multiple doses of drug and $IC_{50}$ values with 95% CI are estimated using linear regression.

Test Procedure for Measuring TACE Inhibition

Using 96-well black microtiter plates, each well receives a solution composed of 10 µL TACE (final concentration 1 µg/mL), 70 µL Tris buffer, pH 7.4 containing 10% glycerol (final concentration 10 mM), and 10 µL of test compound solution in DMSO (final concentration 1 µM, DMSO concentration <1%) and incubated for 10 minutes at room temperature. The reaction is initiated by addition of a fluorescent peptidyl substrate (final concentration 100 µM) to each well and then shaking on a shaker for 5 sec.

The reaction is read (excitation 340 nm, emission 420 nm) for 10 min. and the increase in fluorescence over time is plotted as a linear line. The slope of the line is calculated and represents the reaction rate.

The linearity of the reaction rate is confirmed ($r^2>0.85$). The mean (x±sem) of the control rate is calculated and compared for statistical significance (p<0.05) with drug-treated rates using Dunnett's multiple comparison test. Dose-response relationships can be generate using multiple doses of drug and $IC_{50}$ values with 95% CI are estimated using linear regression.

Human Monocytic THP-1 Cell Differentiation Assay for Soluble Proteins (THP-1 Soluble Protein Assay)

Mitogenic stimulation of THP-1 cells cause differentiation into macrophage like cells with concomitant secretion of tumor necrosis factor (TNF-•) and TNF receptor (TNF-R p75/80 and TNF-R p55/60) and Interleukin-8 (IL-8), among other proteins. In addition, non-stimulated THP-1 cells shed both the p75/80 and the p55/60 receptors over time. The release of membrane bound TNF-α and possibly TNF-R p75/80 and TNF-R p55/60, but not IL-8, is mediated by an enzyme called TNF-α converting enzyme or TACE. This assay can be used to demonstrate either an inhibitory or a stimulatory compound effect on this TACE enzyme and any cytotoxic consequence of such a compound.

THP-1 cells (from ATCC) are a human monocytic cell line which were obtained from the peripheral blood of a one year old male with acute monocytic leukemia. They can be grown in culture and differentiated into macrophage like cells by stimulation with mitogens.

For the assay, THP-1 cells are seeded from an ATCC stock which was previously grown and frozen back at 5×106/ml/vial. One vial is seeded into a T25-flask with 16 mls of RPMI-1640 with glutamax (Gibco) media containing 10% fetal bovine serum, 100 units/ml penicillin, 100 µg/ml streptomycin, and $5 \times 10^{-5}$ M 2-mercapto-ethanol (THP-1 media). Each vial of cells are cultured for about two weeks prior to being used for an assay and then are used for only 4 to 6 weeks to screen compounds. Cells are subcultured on Mondays and Thursdays to a concentration of 1×105/ml.

To perform an assay, the THP-1 cells are co-incubated in a 24 well plate with 50 ml/well of a 24 mg/ml stock of Lipopolysacharide (LPS) (Calbiochem Lot# B13189) at 37,C in 5% $CO_2$ at a concentration of $1.091 \times 10^6$ cells/ml (1.1 ml/well) for a total of 24 hours. At the same time, 50 ml/well of drug, vehicle or THP-1 media is plated in appropriate wells to give a final volume of 1.2 ml/well. Standard and test compounds are dissolved in DMSO at a concentration of 36 mM and diluted from here to the appropriate concentrations in THP-1 media and added to the wells at the beginning of the incubation period to give final concentrations of 100 mM, 30 mM, 10 mM, 3 mM, 1 mM, 300 nM, and 100 nM. Cell exposure to DMSO was limited to 0.1% final concentration. Positive control wells were included in the experiment which had mitogen added but no drug. Vehicle control wells were included as well, which were identical to the positive control wells, except that DMSO was added to give a final concentration of 0.083%. Negative control wells were included in the experiment which had vehicle but no mitogen or drug added to the cells. Compounds can be evaluated for their effect on basal (non-stimulated) shedding of the receptors by replacing the LPS with 50 ml/well of THP-1 media. Plates are placed into an incubator set at 5% CO2 and at 37° C. After 4 hours of incubation, 300 ml/well of tissue culture supernatant (TCS) is removed for use in an TNF-α ELISA. Following 24 hours of incubation, 700 ml/well of TCS is removed and used for analysis in TNF-R p75/80, TNF-R p55/60 and IL-8 ELISAs.

In addition, at the 24 hours timepoint, and the cells for each treatment group are collected by resuspension in 500 µl/well of THP-1 media and transferred into a FACS tube. Two ml/tube of a 0.5 mg/ml stock of propidium iodide (PI) (Boerhinger Mannheim cat. # 1348639) is added. The samples are run on a Becton Dickinson FaxCaliber FLOW cytometry machine and the amount of dye taken up by each cell is measured in the high red wavelength (FL3). Only cells with compromised membranes (dead or dying) can take up PI. The percent of live cells is calculated by the number of cells not stained with PI, divided by the total number of cells in the sample. The viability values calculated for the drug treated groups were compared to the viability value calculated for the vehicle treated mitogen stimulated group ("vehicle positive control") to determine the "percent change from control". This "percent change from control" value is an indicator of drug toxicity.

The quantity of soluble TNF-α, TNF-R p75/80 and TNF-R p55/60 and IL-8 in the TCS of the THP-1 cell cultures are obtained with commercially available ELISAs from R&D Systems, by extrapolation from a standard curve generated with kit standards. The number of cells that either take up or exclude PI are measured by the FLOW cytometry machine and visualized by histograms using commercially available Cytologic software for each treatment group including all controls.

Biological variability in the magnitude of the response of THP-1 cell cultures requires that experiments be compared on the basis of percent change from "vehicle positive control" for each drug concentration. Percent change in each soluble protein evaluated from the "vehicle positive control" was calculated for each compound concentration with the following formula:

$$\% \text{ Change} = \frac{\text{pg/ml(compound)} - \text{pg/ml(veh pos control)}}{\text{pg/ml(veh pos control)} - \text{pg/ml(veh neg control)}} \times 100$$

For the soluble protein (TNF-α, p75/80, p55/60, IL-8) studies under stimulated conditions, the mean pg/ml of duplicate wells were determined and the results expressed as percent change from "vehicle positive control". For the soluble protein (p75/80 and p55/60 receptors) studies under non-stimulated conditions, the mean pg/ml of duplicate wells were determined and the results expressed as percent change from "vehicle positive control" utilizing the following formula:

$$\% \text{ Change} = \frac{\text{pg/ml(compound neg control)} - \text{pg/ml(veh neg control)}}{\text{pg/ml(veh neg control)}} \times 100$$

IC50 values for each compound are calculated by non-linear regression analysis using customized software utilizing the JUMP statistical package.

For the cell viability studies, the viabilities (PI exclusion) of pooled duplicate wells were determined and the results expressed as % change from "vehicle positive control". The viability values calculated for the compound treated groups were compared to the viability value calculated for the "vehicle positive control" to determine "percent change from control" as below. This value "percent change from control" is an indicator of drug toxicity.

$$\% \text{ Change} = \frac{\% \text{ live cells (compound)}}{\% \text{ live cells (veh pos control)}} - 1 \times 100$$

REFERENCES

Bjornberg, F., Lantz, M., Olsson, I., and Gullberg, U. Mechanisms involved in the processing of the p55 and the p75 tumor necrosis factor (TNF) receptors to soluble receptor forms. Lymphokine Cytokine Res. 13:203–211, 1994.

Gatanaga, T., Hwang, C., Gatanaga, M., Cappuccini, F., Yamamoto, R., and Granger, G. The regulation of TNF mRNA synthesis, membrane expression, and release by PMA- and LPS-stimulated human monocytic THP-1 cells in vitro. Cellular Immun. 138:1–10, 1991.

Tsuchiya, S., Yamabe, M., Yamagughi, Y., Kobayashi, Y., Konno, T., and Tada, K. Establishment and characterization of a human acute monocytic leukemia cell line (THP-1). Int. J. Cancer. 26:1711–176, 1980.

Results of the above in vitro matrix metalloproteinase inhibition, TACE inhibition and THP standard pharmacological test procedures are given in Table 1 below.

| Example | MMP-1[a] | MMP-9[a] | MMP-13[a] | TACE[a] | THP[b] |
|---------|---------|---------|----------|--------|--------|
| 7 | 968 | 116 | 80 | 30 | 60 |
| 9 | 1911 | 244 | 150 | 5.9 | 57 |
| 11 | 875 | 33 | 9.2 | 17 | 58 |
| 13 | 2333 | 95 | 34 | 14 | 42 |
| 99 | 956 |  | 27 | 82 | 32 |

[a]IC50 (nM)
[b]% inhibition at 3 μM

Based on the results obtained in the standard pharmacological test procedures described above, the compounds of this invention were shown to be inhibitors of the enzymes MMP-1, MMP-9, MMP-13 and TNF-α converting enzyme (TACE) and are therefore useful in the treatment of disorders such as arthritis, tumor metastasis, tissue ulceration, abnormal wound healing, periodontal disease, graft rejection, insulin resistance, bone disease and HIV infection.

The compounds of this invention are also useful in treating or inhibiting pathological changes mediated by matrix metalloproteinases such as atherosclerosis, atherosclerotic plaque formation, reduction of coronary thrombosis from atherosclerotic plaque rupture, restenosis, MMP-mediated osteopenias, inflammatory diseases of the central nervous system, skin aging, angiogenesis, tumor metastasis, tumor growth, osteoarthritis, rheumatoid arthritis, septic arthritis, corneal ulceration, proteinuria, aneurysmal aortic disease, degenerative cartilage loss following traumatic joint injury, demyelinating diseases of the nervous system, cirrhosis of the liver, glomerular disease of the kidney, premature rupture of fetal membranes, inflammatory bowel disease, age related macular degeneration, diabetic retinopathy, proliferative vitreoretinopathy, retinopathy of prematurity, ocular inflammation, keratoconus, Sjogren's syndrome, myopia, ocular tumors, ocular angiogenesis/neovascularization and corneal graft rejection.

Compounds of this invention may be administered neat or with a pharmaceutical carrier to a patient in need thereof. The pharmaceutical carrier may be solid or liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such a solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferable sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semi-solid emulsions of either the oil in water or water in oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage to be used in the treatment of a specific patient suffering a MMP or TACE dependent condition must be subjectively determined by the attending physician. The variables involved include the severity of the dysfunction, and the size, age, and response pattern of the patient. Treatment will generally be initiated with small dosages less than the optimum dose of the compound. Thereafter the dosage is increased until the optimum effect under the circumstances is reached. Precise dosages for oral, parenteral, nasal, or intrabronchial administration will be determined by the administering physician based on experience with the individual subject treated and standard medical principles.

Preferably the pharmaceutical composition is in unit dosage form, e.g., as tablets or capsules. In such form, the composition is sub-divided in unit dose containing appropriate quantities of the active ingredient; the unit dosage form can be packaged, compositions, for example packed powders, vials, ampoules, prefilled syringes or sachets containing liquids. The unit dosage form can be, for example, a capsule or tablet itself, or it can be the appropriate number of any such compositions in package form.

What is claimed:
1. A compound having the formula:

B wherein B is

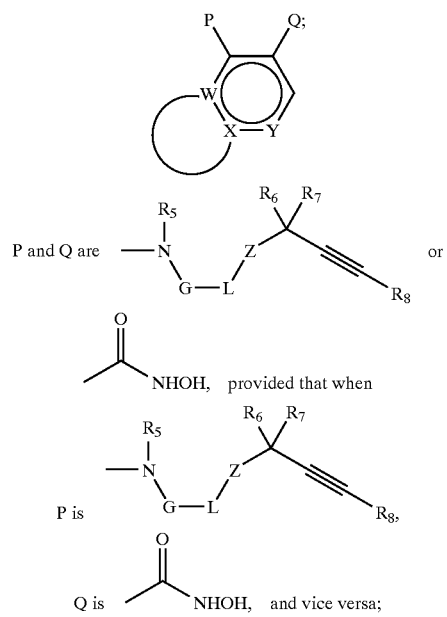

W and X are both carbon;

Y is nitrogen;

G is $SO_2$ or —$P(O)R_4$;

L is a phenyl, naphthyl or heteroaryl, with the proviso that G and Z may not be bonded to adjacent atoms of L;

Z is O, NH, S or $CH_2$;

is a phenyl ring or is a heteroaryl ring selected from:

wherein K is O, $NR_9$ or S;

$R_5$ is hydrogen or alkyl of 1–6 carbon atoms, $R_6$ and $R_7$ are, independently, hydrogen, alkyl of 1–6 carbon atoms, —CN or —CCH;

$R_8$ is hydrogen, alkyl of 1–6 carbon atoms, alkenyl of 2–6 carbon atoms, alkynyl of 2–6 carbon atoms, cycloalkyl of 3–6 carbon atoms, phenyl, naphthyl, or 5 to 10 membered heteroaryl having from 1–3 heteroatoms selected from N, $NR_9$, O and S; and $R_9$ is hydrogen, alkyl of 1–6 carbon atoms, cycloalkyl of 3–6 carbon atoms, or phenyl;

or a pharmaceutically acceptable salt thereof.

2. The compound according to claim 1 wherein:

B is

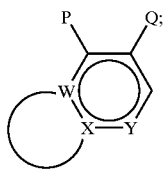

W and X are carbon;

Y is nitrogen;

P is 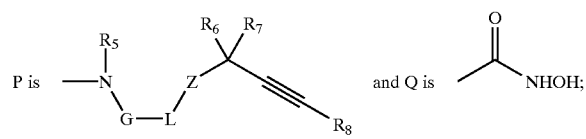 and Q is 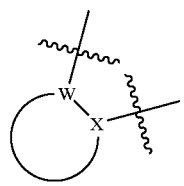

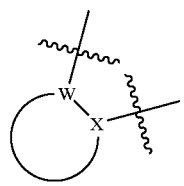

is a phenyl, pyrazole, isoxazole or isothiazole:

or a pharmaceutically acceptable salt thereof.

3. The compound according to clam 2 wherein L is a phenyl ring substituted at the 1- and 4-positions by G and Z, respectively.

4. The compound according to claim 3 wherein G is $SO_2$.

5. The compound according to claim 3 wherein G is $SO_2$ and Z is oxygen.

6. The compound according to claim 3 wherein G is $SO_2$, Z is oxygen, and $R_6$ and $R_7$ are hydrogen.

7. The compound according to claim 3 wherein G is $SO_2$, Z is oxygen, $R_6$ and $R_7$ are hydrogen, and $R_8$ is —$CH_2OH$ or methyl.

8. The compound according to claim 1 which is 4-[(4-But-2-ynyloxy-benzenesulfonyl)-methyl-amino]-1,3-dimethyl-1H-pyrazolo[3,4-b]pyridine-5-carboxylic acid hydroxyamide.

9. The compound according to claim 1 which is 4-[(4-But-2-ynyloxy-benzenesulfonyl)-methyl-amino]-3-methyl-isoxazolo[5,4-b]pyridine-5-carboxylic acid hydroxyamide.

10. The compound according to claim 1 which is 4-[(4-But-2-ynyloxy-benzenesulfonyl)-methyl-amino]-8-methoxy-quinoline-3-carboxylic acid hydroxyamide.

11. The compound according to claim 1 which is 4-[(4-But-2-ynyloxy-benzenesulfonyl)-methyl-amino]-3-methyl-isothiazole[5,4-b]pryidine-5-carboxylic acid hydroxyamide.

12. The compound according to claim 1 which is 8-Bromo-4-[{[4-(2-butynyloxy)phenyl]sulfonyl}(methyl)amino]-N-hydroxy-3-quinolinecarboxamide.

13. A pharmaceutical composition comprising a compound having formula B wherein B is

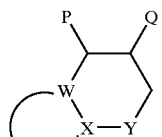

P and Q are 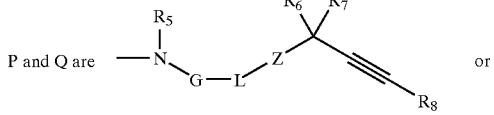 or

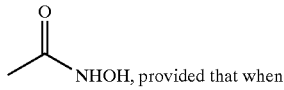, provided that when

P is 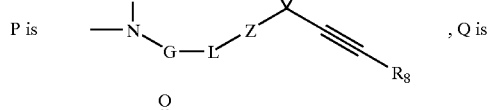, Q is

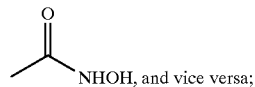, and vice versa;

W and X are both carbon;

Y is nitrogen;

G is $SO_2$ or —$P(O)R_4$;

L is a phenyl, naphthyl or heteroaryl, with the proviso that G and Z may not be bonded to adjacent atoms of L, Z is O, NH, S or $CH_2$;

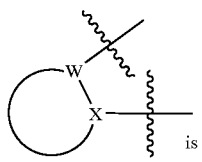 is a phenyl ring or is a heteroaryl ring selected from:

wherein K is O, $NR_9$ or S;

$R_5$ is hydrogen or alkyl of 1–6 carbon atoms, $R_6$ and $R_7$ are, independently, hydrogen, alkyl of 1–6 carbon atoms, —CN or —CCH;

$R_8$ is hydrogen, alkyl of 1–6 carbon atoms, alkenyl of 2–6 carbon atoms, alkynyl of 2–6 carbon atoms, cycloalkyl of 3–6 carbon atoms, phenyl, naphthyl, or 5 to 10 membered heteroaryl having from 1–3 heteroatoms selected from N, $NR_9$, O and S; and $R_9$ is hydrogen, alkyl of 1–6 carbon atoms, cycloalkyl of 3–6 carbon atoms, or phenyl;

or a pharmaceutically acceptable salt thereof; and a pharmaceutically acceptable carrier.

14. A method of treating a patient suffering from rheumatoid arthritis comprising administering to said patient a therapeutically effective amount of a compound having formula B wherein B is

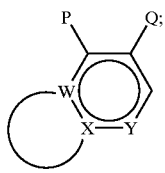

P and Q are

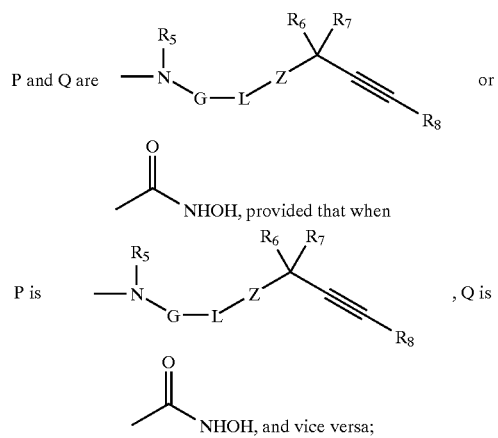

W and X are both carbon;
Y is nitrogen;
G is $SO_2$ or $-P(O)R_4$;

L is a phenyl, naphthyl or heteroaryl, with the proviso that G and Z may not be bonded to adjacent atoms of L, Z is O, NH, S or $CH_2$;

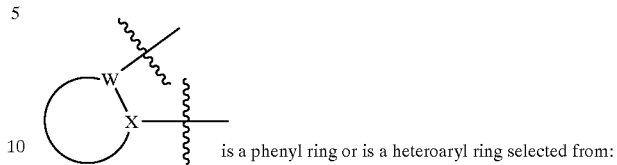 is a phenyl ring or is a heteroaryl ring selected from:

wherein K is O, $NR_9$ or S;

$R_5$ is hydrogen or alkyl of 1–6 carbon atoms, $R_6$ and $R_7$ are, independently, hydrogen, alkyl of 1–6 carbon atoms, —CN or —CCH;

$R_8$ is hydrogen, alkyl of 1–6 carbon atoms, alkenyl of 2–6 carbon atoms, alkynyl of 2–6 carbon atoms, cycloalkyl of 3–6 carbon atoms, phenyl, naphthyl, or 5 to 10 membered heteroaryl having from 1–3 heteroatoms selected from N, $NR_9$, O and S; and $R_9$ is hydrogen, alkyl of 1–6 carbon atoms, cycloalkyl of 3–6 carbon atoms, or phenyl;

or a pharmaceutically acceptable salt thereof.

* * * * *